United States Patent
Reinke et al.

(10) Patent No.: US 7,139,613 B2
(45) Date of Patent: *Nov. 21, 2006

(54) IMPLANTABLE MEDICAL DEVICE COMMUNICATION SYSTEM WITH PULSED POWER BIASING

(75) Inventors: James D. Reinke, Maple Grove, MN (US); Robert M. Ecker, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 458 days.

This patent is subject to a terminal disclaimer.

(21) Appl. No.: 10/733,000

(22) Filed: Dec. 11, 2003

(65) Prior Publication Data

US 2004/0122490 A1 Jun. 24, 2004

Related U.S. Application Data

(63) Continuation-in-part of application No. 10/254,236, filed on Sep. 25, 2002, now Pat. No. 7,013,178.

(51) Int. Cl.
*A61N 1/36* (2006.01)
*A61N 1/378* (2006.01)

(52) U.S. Cl. .............. 607/60; 607/32; 607/2

(58) Field of Classification Search ........... 607/30, 607/32, 34, 60, 61; 128/903
See application file for complete search history.

(56) References Cited

U.S. PATENT DOCUMENTS

| | | | |
|---|---|---|---|
| 3,651,454 A | 3/1972 | Venema et al. | 340/52 F |
| 3,682,160 A | 8/1972 | Murata | 128/2 P |
| 3,717,858 A | 2/1973 | Hadden | 340/203 |
| 3,735,396 A | 5/1973 | Getchell | 340/413 |
| 3,742,473 A | 6/1973 | Hadden | 340/210 |
| 3,805,795 A | 4/1974 | Denniston et al. | 128/419 D |
| 3,857,399 A | 12/1974 | Zacouto | 128/419 P |
| 3,891,914 A | 6/1975 | Akita | 321/47 |
| 3,922,490 A | 11/1975 | Pettis | 179/2 A |
| 3,938,144 A | 2/1976 | Pederson et al. | 340/413 |
| 3,958,558 A | 5/1976 | Dunphy et al. | 128/2 P |

(Continued)

FOREIGN PATENT DOCUMENTS

EP 235 482 A1 9/1987

(Continued)

OTHER PUBLICATIONS

Franklin, et al., "Proposed Standard IEEE P1073 Medical Information Bus Medical Device to Host Computer Interface Network Overview and Architecture", Abstract, CH2713-6/89, pp.574-578.

*Primary Examiner*—Carl Layno
(74) *Attorney, Agent, or Firm*—Girma Wolde-Michael; Daniel G. Chapik

(57) ABSTRACT

An implantable medical device communication system communicates information between an implantable medical device and at least one slave device by way of a two-wire bus. Slave devices may include remote sensors, actuators and other implantable medical devices. The implantable medical device includes a communication unit to output commands and power pulses, and receive information from the slave devices over the two-wire bus. The implantable medical device and slaves communicate over the bus by selectively changing one of the lines of the bus between a first and second voltage, the second voltage substantially equal to a reference voltage of the second line, e.g., zero volts. In some embodiments, the power pulses take the form of bipolar pulse pairs. The slave device includes a recovery unit to recover power from the power pulses.

32 Claims, 30 Drawing Sheets

U.S. PATENT DOCUMENTS

| | | | |
|---|---|---|---|
| 3,959,772 A | 5/1976 | Wakasa et al. | 340/167 A |
| 4,016,480 A | 4/1977 | Hofmann | 323/8 |
| 4,023,562 A | 5/1977 | Hynecek et al. | 128/2.05 E |
| 4,063,220 A | 12/1977 | Metcalfe et al. | 340/147 LP |
| 4,077,030 A | 2/1978 | Helava | 340/183 |
| 4,093,946 A | 6/1978 | Fowler | 340/310 R |
| 4,101,337 A | 7/1978 | Dano | 106/101 |
| 4,114,606 A | 9/1978 | Seylar | 128/2.05 E |
| 4,127,845 A | 11/1978 | Dansbach et al. | 340/151 |
| 4,137,910 A | 2/1979 | Murphy | 128/2.05 R |
| 4,139,737 A | 2/1979 | Shimada et al. | 179/15 AL |
| 4,202,339 A | 5/1980 | Wirtzfeld et al. | 128/419 PG |
| 4,211,238 A | 7/1980 | Shu et al. | 128/700 |
| 4,227,181 A | 10/1980 | Brittain | 340/167 R |
| 4,265,252 A | 5/1981 | Chubbuck et al. | 128/748 |
| 4,266,554 A | 5/1981 | Hamaguri | 128/633 |
| 4,272,758 A | 6/1981 | Giraud | 340/310 A |
| 4,293,947 A | 10/1981 | Brittain | 370/89 |
| 4,311,986 A | 1/1982 | Yee | 340/825.63 |
| 4,360,030 A | 11/1982 | Citron et al. | 128/702 |
| 4,364,397 A | 12/1982 | Citron et al. | 128/710 |
| 4,399,820 A | 8/1983 | Wirtzfeld et al. | 128/419 PG |
| 4,407,296 A | 10/1983 | Anderson | 128/675 |
| 4,413,250 A | 11/1983 | Porter et al. | 340/310 A |
| 4,417,306 A | 11/1983 | Citron et al. | 364/415 |
| 4,420,753 A | 12/1983 | Meyer-Ebrecht | 340/870.26 |
| 4,422,066 A | 12/1983 | Belcourt et al. | 340/500 |
| 4,432,372 A | 2/1984 | Monroe | 128/675 |
| 4,467,807 A | 8/1984 | Bornzin | 128/419 PG |
| 4,485,813 A | 12/1984 | Anderson et al. | 128/675 |
| 4,494,950 A | 1/1985 | Fischell | 604/66 |
| 4,519,401 A | 5/1985 | Ko et al. | 118/748 |
| 4,534,025 A | 8/1985 | Floyd | 370/85 |
| 4,535,401 A | 8/1985 | Penn | 364/132 |
| 4,538,262 A | 8/1985 | Sinniger et al. | 370/85 |
| 4,539,992 A | 9/1985 | Calfee et al. | 128/419 PG |
| 4,543,955 A | 10/1985 | Schroeppel | 128/635 |
| 4,566,456 A | 1/1986 | Koning et al. | 128/419 PG |
| 4,592,364 A | 6/1986 | Pinto | 128/672 |
| 4,600,017 A | 7/1986 | Schroeppel | 128/784 |
| 4,628,934 A | 12/1986 | Pohndorf et al. | 128/419 PG |
| 4,671,288 A | 6/1987 | Gough | 128/635 |
| 4,708,143 A | 11/1987 | Schroeppel | 128/419 PG |
| 4,712,555 A | 12/1987 | Thornander et al. | 128/419 PG |
| 4,716,887 A | 1/1988 | Koning et al. | 128/419 PG |
| 4,730,619 A | 3/1988 | Koning et al. | 128/419 PG |
| 4,738,267 A | 4/1988 | Lazorthes et al. | 128/748 |
| 4,745,596 A | 5/1988 | Sato | 370/85 |
| 4,750,495 A | 6/1988 | Moore et al. | 128/419 PG |
| 4,779,199 A | 10/1988 | Yoneda et al. | 364/413.03 |
| 4,791,935 A | 12/1988 | Baudino et al. | 128/637 |
| 4,794,372 A | 12/1988 | Kazahaya | 340/870.16 |
| 4,802,481 A | 2/1989 | Schroeppel | 128/419 PG |
| 4,807,629 A | 2/1989 | Baudino et al. | 128/419 PG |
| 4,808,994 A | 2/1989 | Riley | 340/825.57 |
| 4,813,421 A | 3/1989 | Baudino et al. | 128/633 |
| 4,815,469 A | 3/1989 | Cohen et al. | 128/634 |
| 4,821,735 A | 4/1989 | Goor et al. | 128/713 |
| 4,827,933 A | 5/1989 | Koning et al. | 128/419 PG |
| 4,841,981 A | 6/1989 | Tanabe et al. | 128/692 |
| 4,846,191 A | 7/1989 | Brockway et al. | 128/748 |
| 4,858,615 A | 8/1989 | Meinema | 128/668 |
| 4,860,751 A | 8/1989 | Callaghan | 128/419 PG |
| 4,867,161 A | 9/1989 | Schaldach | 128/419 PG |
| 4,867,163 A | 9/1989 | Schaldach | 128/419 PG |
| 4,873,980 A | 10/1989 | Schaldach | 128/419 |
| 4,877,032 A | 10/1989 | Heinze et al. | 128/419 PG |
| 4,881,410 A | 11/1989 | Wise et al. | 73/724 |
| 4,886,064 A | 12/1989 | Strandberg | 128/419 PG |
| 4,899,760 A | 2/1990 | Jaeb et al. | 128/696 |
| 4,903,701 A | 2/1990 | Moore et al. | 128/419 PG |
| 4,926,875 A | 5/1990 | Rabinovitz et al. | 128/691 |
| 4,936,304 A | 6/1990 | Kresh et al. | 128/419 PG |
| 4,941,472 A | 7/1990 | Moden et al. | 128/419 PS |
| 4,941,473 A | 7/1990 | Tenerz et al. | 128/637 |
| 4,947,854 A | 8/1990 | Rabinovitz et al. | 128/662.04 |
| 4,967,748 A | 11/1990 | Cohen | 128/419 D |
| 4,967,755 A | 11/1990 | Pohndorf | 128/675 |
| 4,984,572 A | 1/1991 | Cohen | 128/419 D |
| 4,986,270 A | 1/1991 | Cohen | 128/419 D |
| 5,003,976 A | 4/1991 | Alt | 128/419 PG |
| 5,016,631 A | 5/1991 | Hogrefe | 128/419 PS |
| 5,016,641 A | 5/1991 | Schwartz | 128/661.09 |
| 5,021,777 A | 6/1991 | Gross et al. | 340/825.54 |
| 5,025,786 A | 6/1991 | Siegel | 128/642 |
| 5,040,536 A | 8/1991 | Riff | 128/419 PG |
| 5,040,538 A | 8/1991 | Mortazavi | 128/633 |
| 5,058,586 A | 10/1991 | Heinze | 128/634 |
| 5,065,759 A | 11/1991 | Begemann et al. | 128/419 PG |
| 5,076,271 A | 12/1991 | Lekholm et al. | 128/419 PG |
| 5,085,213 A | 2/1992 | Cohen | 128/419 D |
| 5,087,243 A | 2/1992 | Avitall | 604/20 |
| 5,097,831 A | 3/1992 | Lekholm | 128/419 PG |
| 5,109,850 A | 5/1992 | Blanco et al. | 128/635 |
| 5,113,859 A | 5/1992 | Funke | 128/419 PG |
| 5,113,868 A | 5/1992 | Wise et al. | 128/675 |
| 5,129,394 A | 7/1992 | Mehra | 128/419 PG |
| 5,156,157 A | 10/1992 | Valenta, Jr. et al. | 128/662.06 |
| 5,166,678 A | 11/1992 | Warrior | 340/870.15 |
| 5,174,303 A | 12/1992 | Schroeppel | 128/786 |
| 5,184,614 A | 2/1993 | Collins et al. | 128/419 PG |
| 5,186,169 A | 2/1993 | Schaldach | 128/419 PG |
| 5,205,286 A | 4/1993 | Soukup et al. | 128/630 |
| 5,207,103 A | 5/1993 | Wise et al. | 73/724 |
| 5,228,176 A | 7/1993 | Bui et al. | 29/25.35 |
| 5,243,976 A | 9/1993 | Ferek-Petric et al. | 607/6 |
| 5,261,401 A | 11/1993 | Baker et al. | 607/9 |
| 5,265,615 A | 11/1993 | Frank et al. | 128/672 |
| 5,267,564 A | 12/1993 | Barcel et al. | 128/634 |
| 5,275,171 A | 1/1994 | Barcel | 607/122 |
| 5,282,839 A | 2/1994 | Roline et al. | 607/19 |
| 5,293,879 A | 3/1994 | Vonk et al. | 128/782 |
| 5,304,208 A | 4/1994 | Inguaggiato et al. | 607/17 |
| 5,316,001 A | 5/1994 | Ferek-Petric et al. | 128/661.08 |
| 5,324,316 A | 6/1994 | Schulman et al. | 607/61 |
| 5,324,326 A | 6/1994 | Lubin | 607/122 |
| 5,325,870 A | 7/1994 | Kroll et al. | 607/122 |
| 5,330,505 A | 7/1994 | Cohen | 607/6 |
| 5,336,243 A | 8/1994 | Schaldach | 607/18 |
| 5,336,253 A | 8/1994 | Gordon et al. | 607/122 |
| 5,342,404 A | 8/1994 | Alt et al. | 607/6 |
| 5,353,800 A | 10/1994 | Pohndorf et al. | 128/673 |
| 5,358,514 A | 10/1994 | Schulman et al. | 607/61 |
| 5,365,930 A | 11/1994 | Takashima et al. | 128/672 |
| 5,368,040 A | 11/1994 | Carney | 128/700 |
| 5,391,190 A | 2/1995 | Pederson et al. | 607/23 |
| 5,394,400 A | 2/1995 | Phoy | 370/85.1 |
| 5,409,009 A | 4/1995 | Olson | 128/661.08 |
| 5,411,532 A | 5/1995 | Mortazavi | 607/22 |
| 5,417,717 A | 5/1995 | Salo et al. | 607/18 |
| 5,423,869 A | 6/1995 | Poore et al. | 607/18 |
| 5,431,172 A | 7/1995 | Hoegnelid et al. | 128/705 |
| 5,438,987 A | 8/1995 | Thacker et al. | 128/634 |
| 5,451,940 A | 9/1995 | Schneider et al. | 340/870.37 |
| 5,454,838 A | 10/1995 | Vallana et al. | 607/19 |
| 5,464,435 A * | 11/1995 | Neumann | 607/9 |
| 5,470,348 A | 11/1995 | Neubauer et al. | 607/68 |
| 5,474,754 A | 12/1995 | Saxton et al. | 423/705 |
| 5,488,307 A | 1/1996 | Plott | 324/555 |
| 5,490,323 A | 2/1996 | Thacker et al. | 29/625 |
| 5,496,361 A | 3/1996 | Moberg et al. | 607/122 |
| 5,497,772 A | 3/1996 | Schulman et al. | 128/635 |
| 5,499,627 A | 3/1996 | Steuer et al. | 128/633 |
| 5,507,737 A | 4/1996 | Palmskog | 604/891.1 |

| | | | |
|---|---|---|---|
| 5,518,001 A | 5/1996 | Snell | 128/697 |
| 5,535,752 A | 7/1996 | Halperin et al. | 128/670 |
| 5,549,652 A | 8/1996 | McClure et al. | 607/28 |
| 5,564,434 A | 10/1996 | Halperin et al. | 128/748 |
| 5,593,430 A * | 1/1997 | Renger | 607/18 |
| 5,617,235 A | 4/1997 | Abrahamson | 359/142 |
| 5,628,777 A | 5/1997 | Moberg et al. | 607/122 |
| 5,684,451 A | 11/1997 | Seberger et al. | 340/310.06 |
| 5,693,075 A | 12/1997 | Plicchi et al. | 607/17 |
| 5,697,958 A | 12/1997 | Paul et al. | 607/31 |
| 5,700,283 A | 12/1997 | Salo | 607/17 |
| 5,701,895 A | 12/1997 | Prutchi et al. | 128/630 |
| 5,702,427 A | 12/1997 | Ecker et al. | 607/28 |
| 5,715,827 A | 2/1998 | Corl et al. | 128/673 |
| 5,722,996 A | 3/1998 | Bonnet et al. | 607/17 |
| 5,722,998 A | 3/1998 | Prutchi et al. | 607/30 |
| 5,725,562 A | 3/1998 | Sheldon | 607/19 |
| 5,735,883 A | 4/1998 | Paul et al. | 607/28 |
| 5,740,596 A | 4/1998 | Corl et al. | 29/25.35 |
| 5,741,211 A | 4/1998 | Renirie et al. | 600/300 |
| 5,751,154 A | 5/1998 | Tsugai | 324/661 |
| 5,773,270 A | 6/1998 | D'Orazio et al. | 435/177 |
| 5,782,883 A | 7/1998 | Kroll et al. | 607/14 |
| 5,785,657 A | 7/1998 | Breyer et al. | 600/454 |
| 5,791,344 A | 8/1998 | Schulman et al. | 128/635 |
| 5,792,195 A | 8/1998 | Carlson et al. | 607/17 |
| 5,797,395 A | 8/1998 | Marin | 128/673 |
| 5,810,735 A | 9/1998 | Halperin et al. | 600/486 |
| 5,812,802 A | 9/1998 | Bahout et al. | 395/308 |
| 5,836,987 A | 11/1998 | Baumann et al. | 607/17 |
| 5,843,135 A | 12/1998 | Weijand et al. | 607/17 |
| 5,885,471 A | 3/1999 | Ruben et al. | 216/33 |
| 5,899,927 A | 5/1999 | Ecker et al. | 607/23 |
| 5,902,326 A | 5/1999 | Lessar et al. | 607/36 |
| 5,911,738 A | 6/1999 | Sikorski et al. | 607/19 |
| 5,917,346 A | 6/1999 | Gord | 327/101 |
| 5,918,110 A | 6/1999 | Abraham-Fuchs et al. | 438/48 |
| 5,928,344 A | 7/1999 | Stierli | 710/105 |
| 5,935,081 A | 8/1999 | Kadhiresan | 600/513 |
| 5,936,520 A | 8/1999 | Luitje et al. | 340/517 |
| 5,954,752 A | 9/1999 | Mongeon et al. | 607/6 |
| 5,957,957 A | 9/1999 | Sheldon | 607/17 |
| 5,977,431 A | 11/1999 | Knapp et al. | 623/11 |
| 5,977,803 A | 11/1999 | Tsugai et al. | 327/94 |
| 5,985,129 A | 11/1999 | Gough et al. | 205/724 |
| 5,986,497 A | 11/1999 | Tsugai | 327/554 |
| 5,995,860 A | 11/1999 | Sun et al. | 600/341 |
| 5,999,848 A | 12/1999 | Gord et al. | 607/2 |
| 6,002,963 A | 12/1999 | Mouchawar et al. | 607/18 |
| 6,017,313 A | 1/2000 | Bratteli et al. | 600/485 |
| 6,024,704 A | 2/2000 | Meador et al. | 600/486 |
| 6,025,670 A | 2/2000 | Corl et al. | 310/369 |
| 6,038,475 A | 3/2000 | Sikorski et al. | 607/19 |
| 6,038,480 A | 3/2000 | Hrdlicka et al. | 607/116 |
| 6,070,103 A | 5/2000 | Ogden | 607/60 |
| 7,013,178 B1 * | 3/2006 | Reinke et al. | 607/60 |
| 2002/0040234 A1 | 4/2002 | Linberg | 607/32 |
| 2003/0114898 A1 | 6/2003 | Von Arx et al. | 607/60 |

FOREIGN PATENT DOCUMENTS

| | | |
|---|---|---|
| EP | 0 356 603 B1 | 11/1993 |
| EP | 1 040 848 A1 | 8/2003 |

* cited by examiner

Nominally One Bit Time

Fast Sender - Slow Receiver One Bit Time

Slow Sender - Fast Receiver One Bit Time

Master Stop, Master Ack Req, Slave NAK

Slave stop-stop-stop

Message from Master to One or more slaves

A response with data from slave to master

General Command Format

| | msb...lsb | one bit | msb...lsb | msb...lsb | msb...lsb | Stop-AckReq-(N)Ack | |
|---|---|---|---|---|---|---|---|
| Master1 | Master2 | M3 | Master4 | Master5 | Master6 | Master7 | Total Bit Times |
| Start | Slave(s) | QT | Master Command Name | Data | FCS | Stop Sequence | |
| 2 bit times | 6 bit times | 1 bit time | 5 bit times for most commands | 8 bit times for most commands | 8 bit times | 3 bit times | 33 for most Commands |
| | $G_1$ $G_0$ $A_3$ $A_2$ $A_1$ $A_0$ | | | | | | |

FIG. 24

Long Address Format

| 64 bit Long Address | | | | | |
|---|---|---|---|---|---|
| msb...lsb | msb...lsb | msb...lsb | msb...lsb | msb...lsb | msb...lsb |
| 6 Bit Manufacturer Code (up to 64 Manufacturers) $00000_2$ = Medtronic $00001_2$ = Viatron $00010_2$ = MRG | 6 bit Protocol Version (Each manufacturer) can have up to 64 different protocols) | 21 bit Slave Model ID | 20 bit Slave Serial Number (up to 1,048,576 unique slaves) | 7 bit Manufacturing Facility (Manufacturer Specific) ACSII Char V = Medtronic Villalba Puerto Rico ASCII Char R = Medtronic Rice Creek | 4 bit Slave Number (one lead could have 16 slaves) (allows numbering of the slaves on the lead) |

FIG. 25

Slave Short Addresses and Multicast Examples

| Slave Short Address | Master2 |
|---|---|
| | Slave(s) |

| Slave Short Address | $G_1$ | $G_0$ | $A_3$ | $A_2$ | $A_1$ | $A_0$ |
|---|---|---|---|---|---|---|
| 0 | 0 | 0 | 0 | 0 | 0 | 1 |
| 1 | 0 | 0 | 0 | 0 | 1 | 0 |
| 2 | 0 | 0 | 0 | 1 | 0 | 0 |
| 3 | 0 | 0 | 1 | 0 | 0 | 0 |
| 4 | 0 | 1 | 0 | 0 | 0 | 1 |
| 5 | 0 | 1 | 0 | 0 | 1 | 0 |
| 6 | 0 | 1 | 0 | 1 | 0 | 0 |
| 7 | 0 | 1 | 1 | 0 | 0 | 0 |
| 8 | 1 | 0 | 0 | 0 | 0 | 1 |
| 9 | 1 | 0 | 0 | 0 | 1 | 0 |
| A | 1 | 0 | 0 | 1 | 0 | 0 |
| B | 1 | 0 | 1 | 0 | 0 | 0 |
| C | 1 | 1 | 0 | 0 | 0 | 1 |
| D | 1 | 1 | 0 | 0 | 1 | 0 |
| E | 1 | 1 | 0 | 1 | 0 | 0 |
| F | 1 | 1 | 1 | 0 | 0 | 0 |
| Broadcast All | 0 | 0 | 0 | 0 | 0 | 0 |
| Multicast Slaves: 3.2.1.0 | 0 | 0 | 1 | 1 | 1 | 1 |
| Multicast Slaves: 7.5.4 | 0 | 1 | 1 | 0 | 1 | 1 |
| Multicast Slaves: B.A.8 | 1 | 0 | 1 | 1 | 0 | 1 |
| Multicast Slaves: E.D.C | 1 | 1 | 0 | 1 | 1 | 1 |

Command Codes and Measured Parameters

| Command Codes | Measured Parameter | Description |
|---|---|---|
| Vsense | | Command Code that is passed with a trigger down to the Defines the start of the "Pressure Parameter Processing Window". |
| End of Pressure Window | | Command Code that is passed with a trigger down to the sensor. Defines the end of the "Pressure Parameter Processing Window". |
| | max + RV dP / dt | Maximum Positive dP/dt within "Pressure Parameter Processing Window". |
| | min. - RV dP / dt | Minimum Negative dP/dt within "Pressure Parameter Processing Window". |
| | PEI | Pre-Ejection Interval. Time interval from Vsense Command Code to + RV dP / dt point. Calculated from time stamp deltas of triggers. |
| | STI | Systolic Time Interval - Time interval from Vsense Command code to - RV dP dt point. Calculated from time stamp deltas of triggers. |
| | RV Systolic Pressure | Maximum Pressure. Systole is when the heart is squeezing to pump blood. |
| | RV Diastolic Pressure | Ideally Minimum Pressure but will be defined as pressure measured at Vsense trigger Command Code. Diastole is when the heart is relaxed and is filling with blood. |
| | RV Pulse Pressure | RV Systolic - RV Diastolic. |
| | ePAD | Pressure at max + RV dP/dt. ePAD is estimated Pulmonary Artery Diastolic pressure and gives an estimate of a snapshot of left ventricular pressure since the mitral valve is open at this point in time. |

FIG. 31

Command Overview

| Master Command Name | Command Length Bit Times | Command Usage |
|---|---|---|
| Unlocks (00hex) | 33 | Safety command for master to unlock/lock certain areas of memory or to unmap slaves so they only respond to the long addresses. |
| Search Long Address (01hex) | 26-89 (As search progresses more and more of the long address is added onto the command) | Sends a string of bit(s) representing the long address stretching from MSB towards LSB. If a slave is at that long address and is unmapped then it pulls the DATA line low (i.e. does an ack). |
| Write Short Address (02hex) | 89 | Using the long address it assigns a short address |
| Trigger (03hex) | 33 | Triggering slaves. Each trigger has an associated Count and Command Code. |
| Quick Trigger (QT bit Set) | 24 | Triggering slaves with a command fewer bit time. Each trigger has an associated Count. |
| Read (04hex) | 24 plus data response | Reads RAM/ Register Memory |
| Read Results (05hex) | 33 plus data response | Reads Result (ADC) data out of RAM/Register Memory and has an automatic clear data function and resetting of pointer movement. |
| Write (06hex) | 33 | Writes a value into RAM/Register Memory |
| LSB RAM/REG Address (07hex) | 33 | Sets LSB portion of Pointer to RAM/Register Address Space |
| MSB RAM/REG Address (08hex) | 33 | Sets MSB portion of Pointer to RAM/Register Address Space |
| LSB EEPROM Address (09hex) | 33 | Sets LSB portion of Pointer to EEPROM Address Space |
| MSB EEPROM Address (0Ahex) | 33 | Sets MSB portion of Pointer to EEPROM Address Space |
| Copy RAM/REG to EEPROM memory (0Bhex) | 33 | Copies data from RAM/Register Address Space to EEPROM. |
| Copy EEPROM to RAM/REG memory (0Chex) | 33 | Copies data from EEPROM to RAM/Register address space. |
| Quick read (0Dhex) | 33 plus data response | Reads the address pointers for debug. Reads the status by the error code and power monitoring. |
| | | Master Command Names 0Ehex thru 1Fhex are unused. |

FIG. 32

Master's Unlocks (00hex) Command

| Master | Master2 | M3 | Master4 | Master5 | | Master6 | Master7 | Total Bit Times |
|---|---|---|---|---|---|---|---|---|
| Start | Slaves Unicast or Broadcast See Table 16 | QT | Master Commnad Name- Unlocks (00hex) | Unlock Key Code | Unlock Key Option | FCS | Stop-AckReq-(N)Ack | |
| 2 | 6 | 1 | 5 | 5 | 3 | 8 | 3 | 33 |
| | $G_1$ $G_0$ $A_3$ $A_2$ $A_1$ $A_0$ | 0 | | | | | | |
| | | | If Broadcast then all slaves (mapped or unmapped) listen to this command. | | | | | |
| | | | If Unicast and not for this slave then go to sleep after Master2. | | | | | |

FIG. 33

Unlock Key Options

| Master | M3 | Master4 | Master5 | | Explanation | Notes |
|---|---|---|---|---|---|---|
| Slave(s) | QT | Unlocks | Unlock Key Code(1) | Unlock Key Options | | |
| Broadcast Only | 0 | (00hex) | $00111_2$ (07hex) | $000_2$ - Disallow writing a slave long address (and clock/supply trim) $111_2$ - Allow writing a slave long address (and clock/supply trim) | Allows/Disallows setting the memory pointer via the LSB RAM/REG Address (07hex) and MSB RAM/REG Address (08hex) commands to those memory locations that contain the long address (and clock/supply trim) in volatile memory you need to unlock that ability with the copy commands (see below in this table) | (2) |
| Broadcast Only | 0 | | $00001_2$ (01hex) | $000_2$ - Check for unmapped $001_2$ - Check for mapped $111_2$ - Unmap all slaves | Works in conjunction with the Search Long Address (01hex) command If $000_2$ - is sent: "Check for unmapped" any unmapped slave will have an ACK response. If $001_2$ - is sent: "Check for mapped" any mapped slave will have an ACK response. | (3) |
| Unicast Only | 0 | | $01011_2$ (0Bhex) | $000_2$ - Disallow copying $111_2$ - Allow copying | Works in conjunction with the Copy RAM/REG to EEPROM memory (0Bhex) | (4) |
| Unicast Only | 0 | | $01100_2$ (0Chex) | $000_2$ - Disallow copying $111_2$ - Allow copying | Works in conjunction with the Copy EEPROM to RAM/REG memory (0Chex) | (5) |

FIG. 34

Master's Unlocks (00hex) Command

| Master1 | Master2 | M3 | Master4 | Master5 | Master6 | Master7 | Total Bit Times |
|---|---|---|---|---|---|---|---|
| Start | Slaves Broadcast | QT | Master Command Name Search Long Address (01hex) | Long Address | FCS | Stop Ackreq (N) Ack | |
| 2 | 6 | 1 | 5 | 1 to 64 bits | 8 | 3 | 26 to 89 |
| | $G_1$ $G_0$ $A_3$ $A_2$ $A_1$ $A_0$ | 0 | | | | | |
| | | | | All slaves listen to this command whether mapped or unmapped since this command is Broadcast any slave that is mapped does not acknowledge this command see Table 18 (Example Search). A mapped slave may optionally go to sleep after filed Master 4. | | | |

FIG. 35

Example Search

| Step | Slave Long Address Bit Patter (Field Master4) (MSB first) | Slave 1010 response | Slave 1001 response | Found Slave |
|---|---|---|---|---|
| 0 | Send out an Unlocks (00hex) command forcing all the slaves to be unmapped. Skip this step if you are just checking for new slaves added. | | | |
| 1 | Send out an Unlocks (00hex) command checking for any unmapped slaves. The command is ACK'd since Slaves 1010 and 1001 will say they are unmapped. | | | |
| 2 | 1 | ack | ack | |
| 3 | 11 | nak | nak | |
| 4 | 10 | ack | ack | |
| 5 | 101 | ack | nak | |
| 6 | 1011 | nak | nak | |
| 7 | 1010 | ack | nak | 1010 |
| 8 | Send out a Write Short Address (02hex) command to assign 1010 a short address. This will make this slave mapped. | | | |
| 9 | Send out and Unlocks (00hex) command checking for any unmapped slaves. The command is ACK'd since Slave 1001 will say it is unmapped. | | | |
| 10 | 1 | nak (mapped) | ack | |
| 11 | 11 | nak (mapped) | nak | |
| 12 | 10 | nak (mapped) | ack | |
| 13 | 101 | nak (mapped) | nak | |
| 14 | 100 | nak (mapped) | nak | |
| 15 | 1001 | nak (mapped) | ack | 1001 |
| 16 | Send out a Write Short Address (02hex) command to assign 1001 a short address. This will make this slave mapped. | | | |
| 17 | Send out and Unlocks (00hex) command checking for any unmapped slaves. The command is NAK'd since both slaves 1010 and 1001 are mapped. This tells the master the search for unmapped slaves is completed. | | | |

FIG. 36

Master's Write Short Address (02hex) Command

| Master1 | Master2 | M3 | Master4 | Master5 | Master6 | Master7 | Total Bit Times |
|---|---|---|---|---|---|---|---|
| Start | Slaves Unicast | QT | Master Command Name Write Short Address (02hex) | Long Address | FCS | Stop-Ackreq-(N) Ack | |
| 2 | 6 | 1 | 5 | 64 | 8 | 3 | 89 |
| | $G_1$ $G_0$ $A_3$ $A_2$ $A_1$ $A_0$ | 0 | | | | | |
| | | | | | | unmapped Long Address not for this above goes to sleep after Master5 | |
| | | | Mapped - not for this slave go to sleep after Master2 | | | | |

FIG. 37

Trigger (03hex) Command

| Master1 | Master2 | | | | | | M3 | Master4 | Master5 | | Master7 | Master6 | Total Bit Times |
|---|---|---|---|---|---|---|---|---|---|---|---|---|---|
| Start | Slave(s) Multicast | | | | | | QT | Master Command Name-Trigger (o3hex) | Count | Command Code | Stop-AckREq-(N)Ac | FCS | |
| 2 | 6 | | | | | | 1 | 5 | 4 | 4 | 3 | 8 | 33 |
| | $G_1$ | $G_0$ | $A_3$ | $A_2$ | $A_1$ | $A_0$ | 0 | | | | | | |
| | | | | | | | | | unmapped - goes to sleep after Master4 | | | | |
| | | | | | | | | Mapped - not for this slave go to sleep after Master2 | | | | | |

FIG. 38

Trigger Command Code for cardiac IMD

| Trigger Command Code | Code Meaning |
|---|---|
| 0000 | RV Pace |
| 0001 | RV Sense |
| 0010 | RA Pace |
| 0011 | RA Sense |
| 0100 | LV Pace |
| 0101 | LV Sense |
| 0110 | LA Pace |
| 0111 | LA Sense |
| 1000 | unused |
| 1001 | unused |
| ... | unused... |
| 1110 | no specific Command Code occurring |
| 1111 | Cleared Data |

FIG. 39

Trigger Command Code for Sonomicrometry

| Trigger Command Code | Code Meaning |
|---|---|
| 0000 | all listen external acoustic ping |
| 0001 | acoustic ping 0 listen 1,2,3,4 |
| 0010 | acoustic ping 1 listen 0,2,3,4 |
| 0011 | acoustic ping 2 listen 0,1,3,4 |
| 0100 | acoustic ping 3 listen 0,1,2,4 |
| 0101 | acoustic ping 4 listen 0,1,2,3 |
| 0110 | TBD or error or unused do nothing |
| 0111 | TBD or error or unused do nothing |
| ... | TBD or error or unused do nothing |
| 1110 | no specific Command Code occurring -don't reconfigure |
| 1111 | Cleared Data |

FIG. 40

Quick Trigger (QT bit Set) Command

| Master1 | Master2 | | | | | | M3 | Master4 | Master5 | Master6 | Total Bit Times |
|---|---|---|---|---|---|---|---|---|---|---|---|
| Start | Slaves | | | | | | QT | Count | FCS | Stop-AckReq-(N)Ack | |
| 2 | 6 | | | | | | 1 | 4 | 8 | 3 | 24 |
| | $G_1$ | $G_0$ | $A_3$ | $A_2$ | $A_1$ | $A_0$ | 1 | | | | |
| | | | | | | | | unmapped - goes to sleep after Master3 | | | |
| | | | | | | | | Mapped - not for this slave go to sleep after Master2 | | | |

FIG. 41

Master's Write Short Address (02hex) Command

| Master1 | Master2 | | | | | | M3 | Master4 | Master5 | Master6 | Master7 | Total Bit Times |
|---|---|---|---|---|---|---|---|---|---|---|---|---|
| Start | Slaves Unicast | | | | | | QT | Master Command Name Read (04hex) | Quantity of bytes 1 | FCS | Stop-Ackreq-(N) Ack (Slave Ack Master) | |
| 2 | 6 | | | | | | 1 | 5 | 8 | 8 | 3 | 24 |
| | $G_1$ | $G_0$ | $A_3$ | $A_2$ | $A_1$ | $A_0$ | 0 | | | | | |
| | | | | | | | | | unmapped - goes to sleep after Master4 | | | |
| | | | | | | | | Mapped - not for this slave go to sleep after Master2 | | | | |

FIG. 42

Slave's Read (04hex) Response

| msb...lsb | msb...lsb | msb...lsb | msb...lsb | msb...lsb | msb...lsb | msb...lsb |
|---|---|---|---|---|---|---|
| Slave 0 | Slave 1 | Slave... | Slave x-3 | Slave x-2 | Slave x-1 | Slave x |
| Data byte 0 | Data byte 1 | Data... (multiple bytes) | Data byte n-2 | Data byte n-1 | FCS | Stop-Stop-Stop |

FIG. 43

Rules for Read Results (05hex) command

| | Read Results (05hex) command is told to read Buffer 0 | Read Results (05hex) command is told to read Buffer 1 |
|---|---|---|
| If ADC Pointer is currently set to write to Buffer 0 | 1. Set Buffer 1's Count and/or Command Codes to $F_{16}$ codes and have ADC point to top of Buffer 1. Data Result Values of Buffer 1 may or may not be cleared to F codes - this is slave dependent since may want to leave alone to save power.<br>2. Set Read Result Pointer to Top of Buffer 0.<br>3. Send up contents of Buffer 0 for quantity of bytes requested. | (Must be a retry re-read of Buffer 0)<br>1. Continue ADC writing Buffer 0<br>2. Set Read Result Pointer Top of Buffer 1.<br>3. Send up contents of Buffer 1 for quantity of bytes requested. |
| If ADC Pointer is currently set to write to Buffer 1 | (Must be a retry re-read of Buffer 0)<br>1. Continue ADC writing Buffer 1.<br>2. Set Read Result Pointer Top of Buffer 0.<br>3. Send up contents of Buffer 0 for quantity of bytes requested. | 1. Set Buffer 0's Count and/or Command Codes to $F_{16}$ codes and have ADC point to top of Buffer 0. Data Result Values of Buffer 0 may or may not be cleared to F codes - this is slave dependent since may want to leave alone to save power.<br>2. Set Read Result Pointer to Top of Buffer 1.<br>3. Send up contents of Buffer 1 for quantity of bytes requested. |

FIG. 44

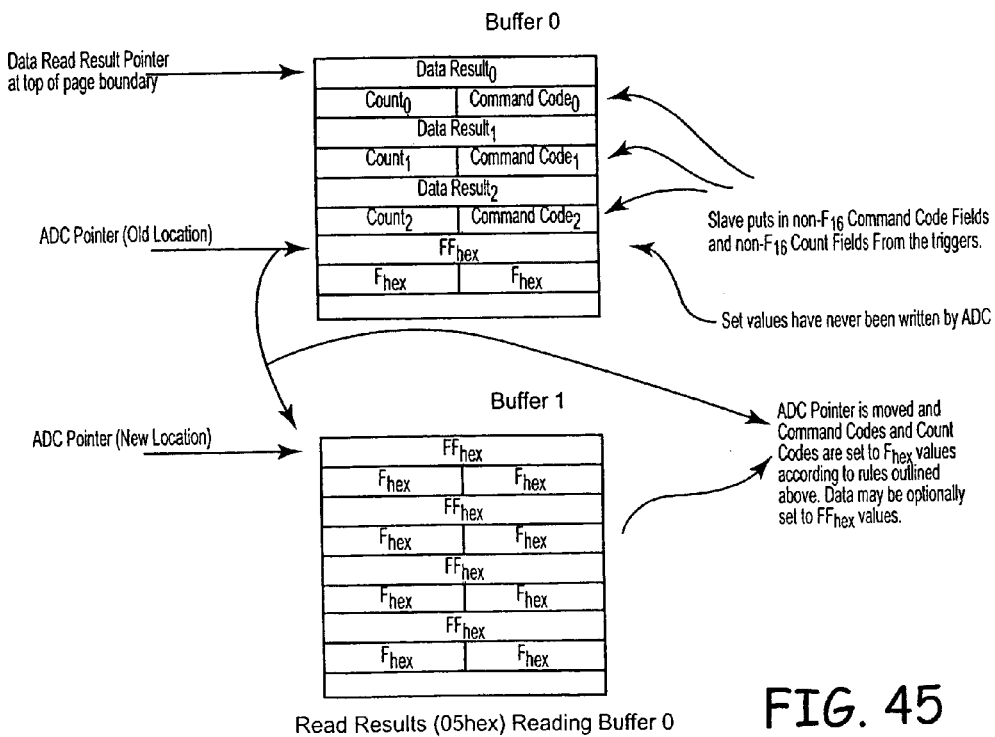

FIG. 45

Master's Road Results (05hex) Command

| Master1 | Master2 | M3 | Master4 | Master5 | | M6 | Master7 | Total Bit Times |
|---|---|---|---|---|---|---|---|---|
| Start | Slave | QT | More Command Name - | Buffer | Quantity of | FCS | Stop-AckREq-(N)Ack | |
| 2 | 6 | 1 | 5 | 1 | 7 | 8 | 3 | 33 |
| | $G_1$ $G_0$ $A_3$ $A_2$ $A_1$ $A_0$ | 1 | | | | | | |
| | | | | unmapped - goes to sleep after Master4 | | | | |
| | | | Mapped - not for this slave go to sleep after Master2 | | | | | |

FIG. 46

Slave's Read Results (05hex) Example Response

| msb...lsb | msb...lsb | msb...lsb | msb...lsb | msb...lsb | msb...lsb | msb...lsb | msb...lsb | |
|---|---|---|---|---|---|---|---|---|
| Slave 1 | Slave 2 | | Slave... | Slave x-3 | Slave x-2 | | Slave x-1 | Slave x |
| $Data_0$ | $Count_0$ | Command $Code_0$ | (multiple bytes)... | $Data_n$ | $Count_n$ | Command $Code_n$ | FCS | Stop-Stop-Stop |

FIG. 47

Master's Write (06hex) Command

| Master1 | Master2 | M3 | Master4 | Master5 | M6 | Master7 | Total Bit Times |
|---|---|---|---|---|---|---|---|
| Start | Slave Unicast Preferred (Acknowledge will have value) | QT | Master Command Name- White (06hex) | Value Byte to write | FCS | Stop-AckREq-(N)Ack (slave ACK master) | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | unmapped - goes to sleep after Master4 | | | |
| | | | Mapped - not for this slave go to sleep after Master2 | | | | |

FIG. 48

Master's LSB RAM/REG Address (07hex) Command

| Master1 | Master2 | M3 | Master4 | Master5 | M6 | Master7 | Total Bit Times |
|---|---|---|---|---|---|---|---|
| Start | Slave Unicast Preferred (Acknowledge will then have value) | QT | Master Command Name- LSB RAM/REG Address (07hex) | LSB Value | FCS | Stop-AckREq-(N)Ack (slave ACK master) | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | unmapped - goes to sleep after Master4 | | | |
| | | | Mapped - not for this slave go to sleep after Master2 | | | | |

FIG. 49

Master's MSB RAM/REG Address (08hex) Command

| Master1 | Master2 | M3 | Master4 | Master5 | M6 | Master7 | Total Bit Times |
|---|---|---|---|---|---|---|---|
| Start | Slave Unicast Preferred (Acknowledge will have value) | QT | Master Command Name- MSB RAM/REG Address (08hex) | MSB Value Byte to write | FCS | Stop-AckREq-(N)Ack | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | | unmapped - goes to sleep after Master4 | | |
| | | | | Mapped - not for this slave go to sleep after Master2 | | | |

FIG. 50

Master's LSB EEPROM Address (09hex) Command

| Master1 | Master2 | M3 | Master4 | Master5 | M6 | Master7 | Total Bit Times |
|---|---|---|---|---|---|---|---|
| Start | Slave Unicast Preferred (Acknowledge will then have value) | QT | Master Command Name- LSB EEPROM Address (09hex) | LSB Value | FCS | Stop-AckREq-(N)Ack | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | | unmapped - goes to sleep after Master4 | | |
| | | | | Mapped - not for this slave go to sleep after Master2 | | | |

FIG. 51

Master's MSB EEPROM Address (0Ahex) Command

| Master1 | Master2 | M3 | Master4 | Master5 | M6 | Master7 | Total Bit Times |
|---|---|---|---|---|---|---|---|
| Start | Slave Unicast Preferred (Acknowledge will then have value) | QT | Master Command Name- MSB EEPROM Address (0Ahex) | MSB Value | FCS | Stop-AckREq-(N)Ack | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | | unmapped - goes to sleep after Master4 | | |
| | | | | Mapped - not for this slave go to sleep after Master2 | | | |

FIG. 52

Master's copy RAM/REG to EEPROM memory (0Bhex) Command

| Master1 | Master2 | M3 | Master4 | Master5 | M6 | Master7 | Total Bit Times |
|---|---|---|---|---|---|---|---|
| Start | Slave Unicast Preferred (Acknowledge will then have value) | QT | Master Command Name- Copy RAM/REG to EEPROM memory (0Bhex) | Quantity of Bytes 1 | FCS | Stop-AckREq-(N)Ack | |
| 2 | 6 | 1 | 5 | 8 | 8 | 3 | 33 |
| | $G_1$ $G_0$ $A_3$ $A_2$ $A_1$ $A_0$ | 0 | | | | | |
| | | | | | unmapped - goes to sleep after Master4 | | |
| | | | | Mapped - not for this slave go to sleep after Master2 | | | |

FIG. 53

Master's copy to EEPROM to RAM/REG Memory (0Chex) Command

| Master1 | Master2 | | | | | | M3 | Master4 | Master5 | M6 | Master7 | Total Bit Times |
|---|---|---|---|---|---|---|---|---|---|---|---|---|
| Start | Slave Unicast Preferred (Acknowledge will then have value) | | | | | | QT | Master Command Name- Copy to EEPROM to RAM/REG memory (0Chex) | Quantity of Bytes-1 | FCS | Stop-AckREq-(N)Ack | |
| 2 | 6 | | | | | | 1 | 5 | 8 | 8 | 3 | 33 |
| | $G_1$ | $G_0$ | $A_3$ | $A_2$ | $A_1$ | $A_0$ | 0 | | | | | |
| | | | | | | | | | unmapped - goes to sleep after Master4 | | | |
| | | | | | | | | Mapped - not for this slave go to sleep after Master2 | | | | |

FIG. 54

Master's Quick Read (0Dhex) Command

| Master1 | Master2 | | | | | | M3 | Master4 | Master5 | M6 | Master7 | Total Bit Times |
|---|---|---|---|---|---|---|---|---|---|---|---|---|
| Start | Slave Unicast | | | | | | QT | Master Command Name- Quick Read (0Dhex) | QRAddress | FCS | Stop-AckREq-(N)Ack | |
| 2 | 6 | | | | | | 1 | 5 | 8 | 8 | 3 | 33 |
| | $G_1$ | $G_0$ | $A_3$ | $A_2$ | $A_1$ | $A_0$ | 0 | | | | | |
| | | | | | | | | | unmapped - goes to sleep after Master4 | | | |
| | | | | | | | | Mapped - not for this slave go to sleep after Master2 | | | | |

FIG. 55

Master's Which Pointer to Read

| Master5 | Description of what it points to |
|---|---|
| QRAddress | |
| $00_{16}$ | EEPROM Address Pointer |
| $01_{16}$ | RAM Register Space Address Pointer |
| $02_{16}$ | ADC Address Buffer Pointer |
| $03_{16}$ | Status Word |

FIG. 56

Slave's Quick Read (0Dhex) Response

| msb...lasb | msb...lasb | msb...lasb | msb...lasb |
|---|---|---|---|
| Slave 1 | Slave 2 | Slave 3 | Slave 4 |
| Data | Data | FCS | Stop-Stop-Stop |
| MSB | LSB | | |

FIG. 57

Power and data pulses on two-wire bus

Example of power and data sequence with Start and Stop sequences

Example of streaming messages

IMPLANTABLE MEDICAL DEVICE COMMUNICATION SYSTEM WITH PULSED POWER BIASING

This application is a continuation-in-part of U.S. application Ser. No. 10/254,236, filed Sep. 25, 2002 now U.S. Pat. No. 7,013,178, which is herein incorporated by reference in its entirety.

FIELD OF THE INVENTION

The present invention relates to an interface for communication between primary and secondary devices along a two-wire communication bus. More particularly, the present invention relates to an interface for bidirectional communication between an implantable medical device and a plurality of slave devices such as sensors or actuators along a two-wire communication bus.

BACKGROUND OF THE INVENTION

Implantable medical devices take many forms to provide therapy to a patient. For example, implantable medical devices provide pacing therapy to assist in maintaining proper heart rhythm. Pacing therapy may be applied to treat a number of conditions, such as atrial fibrillation, atrial tachyarrhythmia, atrial arrhythmias, ventricular fibrillation, ventricular tachyarrhythmia, and bradyarrhythmias caused by heart block or sinus node dysfunction. Implantable medical devices may also take the form of an implantable cardioverter defibrillator to provide therapy for sudden cardiac arrest, ventricular tachycardia, and ventricular fibrillation.

In order to provide therapy, an implantable medical device ("IMD") communicates with a plurality of implantable slave devices, such as sensors, to monitor conditions including heart electrical activity and blood oxygen content, for example. Both the sensors and the implantable medical device are implanted within the body, and in order to reduce interference to the body, the implantable medical device communicates with the sensors over a small bus having a minimum number of electrically conductive wires. For example, communication information, along with power and ground, is provided over two conductive wires. At the same time, the implantable medical device operates by way of an internal power source, usually in the form of a battery, which has a limited amount of available power. Moreover, because replacement of the implantable medical device requires surgery to the patient, conservation of power is an important consideration.

Implantable medical devices are often required to deliver life-supporting therapy in the form of electrical stimulation to the patient. Accordingly, reliable communication between the implantable medical device and the implantable sensors external to the IMD is important. Furthermore, physical characteristics such as reduced size and space of the devices are desired in order to decrease patient stress, simplify implant procedures, and reduce surgical complications.

SUMMARY OF THE INVENTION

The present implantable medical device communication system includes an implantable medical device ("IMD") running a master clock. Slave devices resynchronize to the IMD clock on the rising edge. The sensor interface improves the data communication rate and permits simultaneous or individual communication with a plurality of external sensors. A 2-wire bus provides power, clock, and data from a single master to up to 16 slave devices. Half-duplex communication and pulse width modulation of the voltage on the bus allow a raw data rate of approximately 100 Kbps. The data is encoded as "1's" and "0's" for data transmission between the master and slave devices. An initialization procedure determines the long address of each slave device and assigns a short address to reduce command length.

A message initiated by the master triggers slave measurements. The master writes data to the slave and the master reads data from the slave. Addressing modes allow individual devices, groups of devices, or all devices to be addressed. The message format includes start, command word, address, data, cyclical redundancy check (CRC), and stop. Cyclical redundancy checking is an error-checking scheme used to check for errors in messages sent by the master and the data response from the slaves. Messages may be selectively acknowledged or selectively not acknowledged by the recipient device, however the master device initiates data communications. Slave devices do not put data on the bus without the master first requesting the data.

The start of a data bit in a message begins with the master pulling the data wire of the two-wire bus up to a high voltage. A fraction of a bit time later, the master pulls the data wire low, such that the duration of the high voltage pulse determines the data value. The master is the only device on the two-wire bus with pull-up capability. The slaves may include a number of implantable devices such as sensors, actuators or slave implantable medical devices ("IMDs").

In some embodiments, the IMD delivers power to the slaves in the form of a DC bias on the bus. In other embodiments, the IMD delivers power to slaves in the form of periodic voltage pulses, such as bipolar voltage pulse pairs, and does not place a DC bias on the bus. In embodiments where the IMD delivers power in the form of pulses, corrosion and other types of electrochemical degradation of bus that are attributable to the presence of DC voltages and conductive solutions can be reduced or eliminated.

In various embodiments of the invention, the IMD delivers one or more power pulses without issuing a command to a slave device, one or more power pulses preceding each command, or one or more power pulses followed by a series of commands to one or more slave devices. In some embodiments in which one or more power pulses precede a command, the polarity of an immediately preceding power pulse indicates the polarity of the data pulses that will follow the command to the slave devices. In such embodiments, the master, for example, generates positive data pulses following a bipolar power pulse pair in which the second pulse of the pair is positive.

Each command is preceded by a start sequence for the message, which includes a forced "0" followed by two logic "1's". Power pulses "wake up" the slaves from a low power state, and cause the slaves to monitor for a start sequence. In some embodiments, power pulses cause slaves to perform a measurement without the need to receive a command.

Each command is followed by a master stop sequence, which includes one bit time for slaves to indicate whether the CRC check passed, e.g., that the message was error-free according to the CRC error check contained in the Frame Check Sequence field of the command. Specifically, slave acknowledge (ACK) that the CRC check passed by pulling a line of the bus low at a first time during the bit to indicate a logic "0", or not acknowledge (NAK) that the CRC check passed by either pulling the line of the bus low at a second time during the bit time to indicate a logic "1" or allowing the line to remain high throughout the first and second times of the bit time, i.e., not responding.

The master stop sequence also includes one bit time for slaves to indicate a power status. Specifically, slaves acknowledge (ACK) a low power status, i.e., indicate that they have low power, by pulling a line of the bus low at a first time during the bit time to indicate a logic "1", or not acknowledge (NAK) the low power status, i.e., indicate that they have adequate power, by either pulling the line of the bus low at a second time during the bit time to indicate a logic "0", or allowing the line to remain high through the first and second times of the bit time, i.e., not responding. The master can output more power pulses in response to detection of a low power ACK.

The master can drive the bus low to signal a data "1" or NACK in embodiments where sensors do not respond during either of the CRC ACK/NACK and Low Power ACK/NACK bit times. By driving the bus low in these situations, the master provides another rising edge for the clock derivation, which can allow sensors to remain synchronized with the master.

BRIEF DESCRIPTION OF THE DRAWINGS

FIG. 24 is a general command format for transferring data across a two-wire bus;

FIG. 25 is a table providing a slave long address format;

FIG. 31 is a table illustrating Command Codes and measured parameters;

FIG. 32 is a table providing a command overview of a sensor interface for an implantable medical device;

FIG. 33 is a table illustrating a Master's Unlocks command;

FIG. 34 is a table illustrating Unlock key options;

FIG. 35 is a table illustrating a Master's Search Long Address command;

FIG. 36 is table summarizing an example search across a sensor for an implantable medical device;

FIG. 37 is a table illustrating a Master's Write Short Address command;

FIG. 38 is a table illustrating a Trigger command;

FIG. 39 is a table illustrating a Trigger Command Code for a cardiac IMD;

FIG. 40 is a table illustrating an example of a Trigger Command Code for Sonomicrometry transmitters and receivers;

FIG. 41 is a table illustrating a Quick Trigger command;

FIG. 42 is a table illustrating a Master's Read command;

FIG. 43 is a table illustrating a Slave's Read Response;

FIG. 44 is a table providing rules for a Read Results command;

FIG. 45 is a pair of tables illustrating an example of reading results from a reading buffer with 8 bit data and a count and a command code embedded;

FIG. 46 is a table illustrating a Master's Read Results command;

FIG. 47 is a table illustrating a Slave's Read Results example response;

FIG. 48 is a table illustrating a Master's Write command;

FIG. 49 is a table illustrating a Master's LSB RAM/REG Address command;

FIG. 50 is a table illustrating a Master's MSB RAM/REG Address command;

FIG. 51 is a table illustrating an LSB EEPROM Address command;

FIG. 52 is a table illustrating a MSB EEPROM Address command;

FIG. 53 is a table illustrating a Master's Copy RAM/REG to EEPROM memory command;

FIG. 54 is a table illustrating a Master's Copy of EEPROM to RAM/REG memory command;

FIG. 55 is a table illustrating a Master's Quick Read command;

FIG. 56 is a table illustrating a Master's Which Pointer to Read command;

FIG. 57 is a Slave's Quick Read Response command;

DETAILED DESCRIPTION

Figure 1:
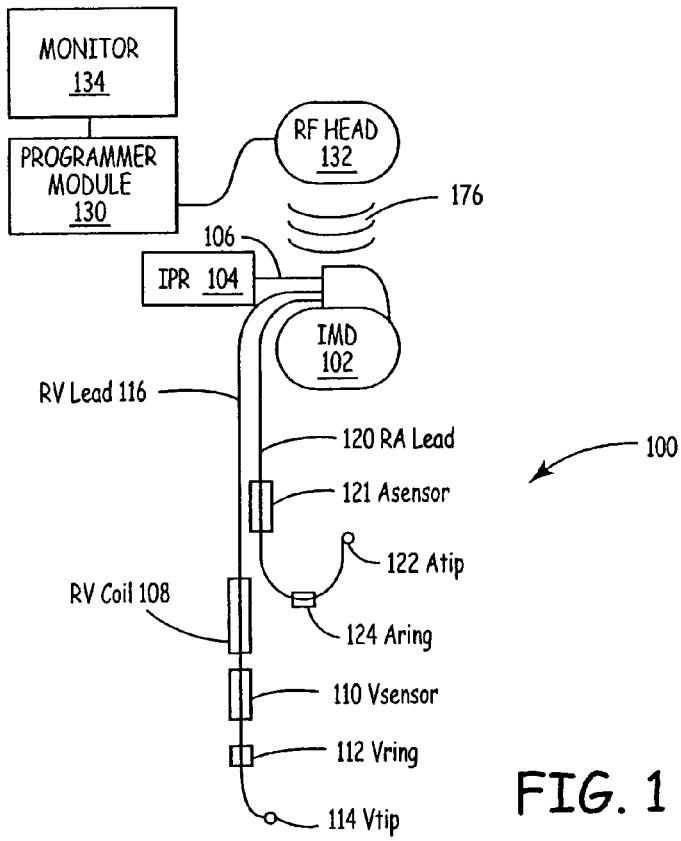
FIG. 1 is a schematic diagram of an implantable medical device system according to an embodiment of the invention.

With reference now to the drawings, wherein like numbers refer to like elements throughout, embodiments of the invention are now described. FIG. 1 is a schematic diagram of an implantable medical device system 100 according to an embodiment of the invention. As illustrated, implantable medical device ("IMD") 102 takes the form of an internal cardio defibrillator or pacemaker, for example, with implantable pressure reference, right ventricular ("RV") pressure, and RV oxygen. System 100 includes IMD 102 that communicates with internal pressure reference ("IPR") 104 by way of communication bus 106.

IMD 102 is electrically connected with right ventricular coil ("RV coil") 108, Vsensor 110, Vring 112, and Vtip 114 by way of right ventricular lead ("RV lead") 116. The RV lead 116 has a true bipolar lead (Vtip 114, Vring 112) for differential sensing, along with a Vsensor capsule 110, and RV Coil 108 for high voltage defibrillation therapy. The Vsensor capsule 110 contains a pressure sensor, an oxygen sensor, and a temperature sensor. The right atrial lead ("RA Lead") 120 is connected to Asensor 121, and a true bipolar lead (Atip 122, Aring 124).

In some embodiments, a DC bias voltage of 3.0 V is maintained across RV Lead 116, and data in the form of 200 mV fluctuations are communicated on top of the 3.0 V bias. In other embodiments, IMD 102 delivers biphasic power pulse pairs (+/−3.0 V) via RV Lead 116, and data in the form of 200 mV pulses are communicated between power pulses. The communication across the two-wire bus of system 100 in one embodiment seeks to minimize resistance, minimize capacitance, minimize inductance, maximize shielding and maximize reliability. The shielding is most easily maximized in a coaxial implementation with a grounded outer conductor and data/clock/power on the inner conductor.

IPR 104 has a separate lead whose communication bus 106 is hooked in parallel with the other communication busses in RV Lead 116 and RA Lead 120. These all share a common pair of feedthrus into IMD 102. Pressure sensors are absolute pressure sensors that require temperature measurement capability. Accordingly, pressure changes in a capsule due to temperature effects are calibrated out.

The sensors are optionally electrically connected in parallel with IMD 102 through a number of different ways. In this embodiment, each lead is plugged into a corresponding port in a connector block and electrical connections between the sensors are made inside the connector. In other embodiments, sensors are serially connected to IMD 102 via the bus. In such embodiments, each of sensors 110 and 121 are, for example, connected by respective pairs of wires to a common connector block port.

Programmer module 130 communicates with IMD 102 by way of RF Link 176 from RF Head 132. The programmer module 130 programs parameters, read status, read diagnostic data and stored waveforms, as well as real-time waveform data. IMD 102 collects data from IPR 104, an oxygen sensor, and temperature sensors at regular intervals on the order of every couple of seconds. Data is further collected from Vsensor 110 at rates up to 2048 samples per second, assuming 16 bit data, and 4 count and 8 bit CRC returned as data. Higher sampling rates can be accomplished by increasing the speed of the bus or decreasing the amount of data sent. Information received from IMD 102 is displayed on programmer module 130 by way of monitor 134.

Figure 2:
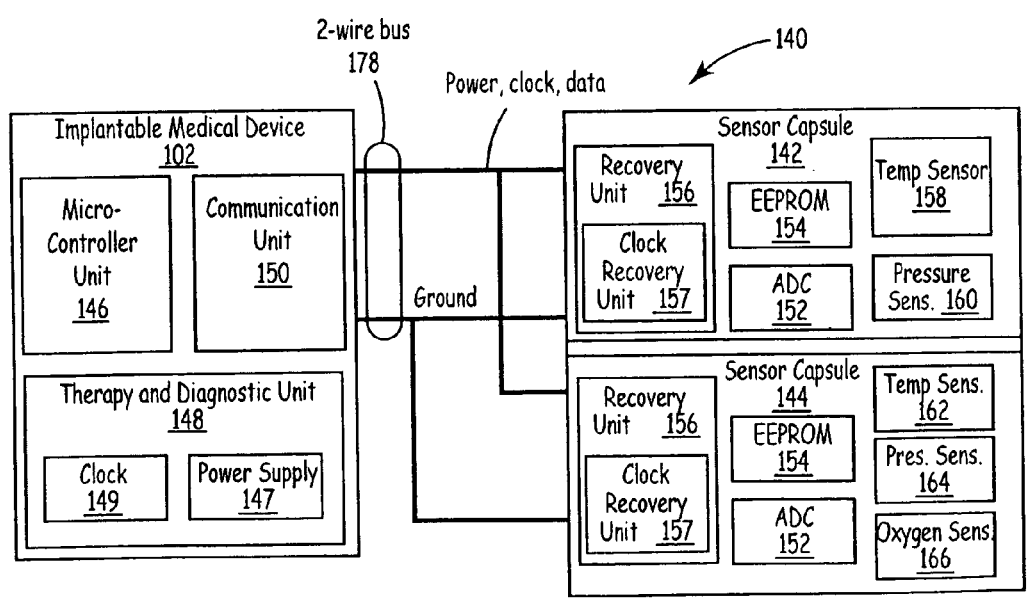
FIG. 2 is a block diagram of an implantable medical device connected to a pair of sensor capsules.

FIG. 2 is a block diagram of an implantable medical device system 140 including IMD 102 connected to sensor capsules 142 and 144 by way of two-wire bus 178. The diagram schematically illustrates parallel electrical connection of sensor capsules 142 and 144 to IMD 102 with each capsule containing more than one sensor.

IMD 102 includes micro-controller unit 146, which has a microcontroller memory (RAM, ROM, EEPROM), telemetry port, and therapy circuitry (for pacing, sensing, defibrillation, and timing). Therapy and diagnostic unit 148 provides an accelerometer and minute ventilation, diagnostic circuitry (electro-gram, waveform compression, battery monitoring, and lead monitoring), and basic infrastructure circuitry (power supply generation, ADC, and references, etc.). Clock 149 is provided within therapy and diagnostic unit 148 to provide timing to IMD 102 and the sensor capsules. Power supply 147 is also provided within therapy and diagnostic unit 148 to provide power to IMD 102 as well as external sensor capsules 142 and 144.

Communication unit 150 communicates with remote sensors and sends power as well as a synchronizing signal or clock signal to remote sensors. Communication unit 150 also contains a transceiver to transmit and receive data over a two-wire communication bus. Communication unit 150 has protection networks to protect IMD 102 against transient voltages and currents induced on two-wire bus 178 due to electro-surgery, electrical discharge, defibrillation, electro-static discharge, electromagnetic interference, etc.

Each sensor capsule 142 and 144 contains circuitry to measure and convert pressure, temperature, and oxygen signals into a digital signal through analog to digital converters ("ADCs") 152. Each sensor capsule (142, 144) also contains a small non-volatile memory, in the form of EEPROM 154, to store a unique sensor address, serial number, and calibration coefficients, etc. Recovery units 156 recover power from the fluctuating voltages on two-wire bus 178 to power each respective sensor.

Clock synchronization allows a relatively inaccurate high speed clock recovery unit 157 to be available on each sensor, which is periodically synchronized with clock 149 on IMD 102. IMD 102 thereby controls the sampling rate and sampling time for each of the individual sensors by way of transmitting commands to the sensor(s), thereby instructing the sensor(s) to sample. IMD 102 also controls when each sensor puts each bit of data on the bus. The need for high accuracy clock generation circuits within each sensor capsule is therefore eliminated. A protection network is also included in each sensor capsule to minimize the effect of transient voltages and currents induced on the two-wire bus 178 due to electro-surgery, implantable cardio defibrillator ("ICD") discharge, defibrillation, electro-static discharge, and electromagnetic interference, etc. As illustrated, sensor capsule 142 includes temp sensor 158 and pressure sensor 160. Likewise, sensor capsule 144 includes temp sensor 162, pressure sensor 164, and oxygen sensor 166. Other sensors may be similarly used in various embodiments of the invention.

Figure 3:
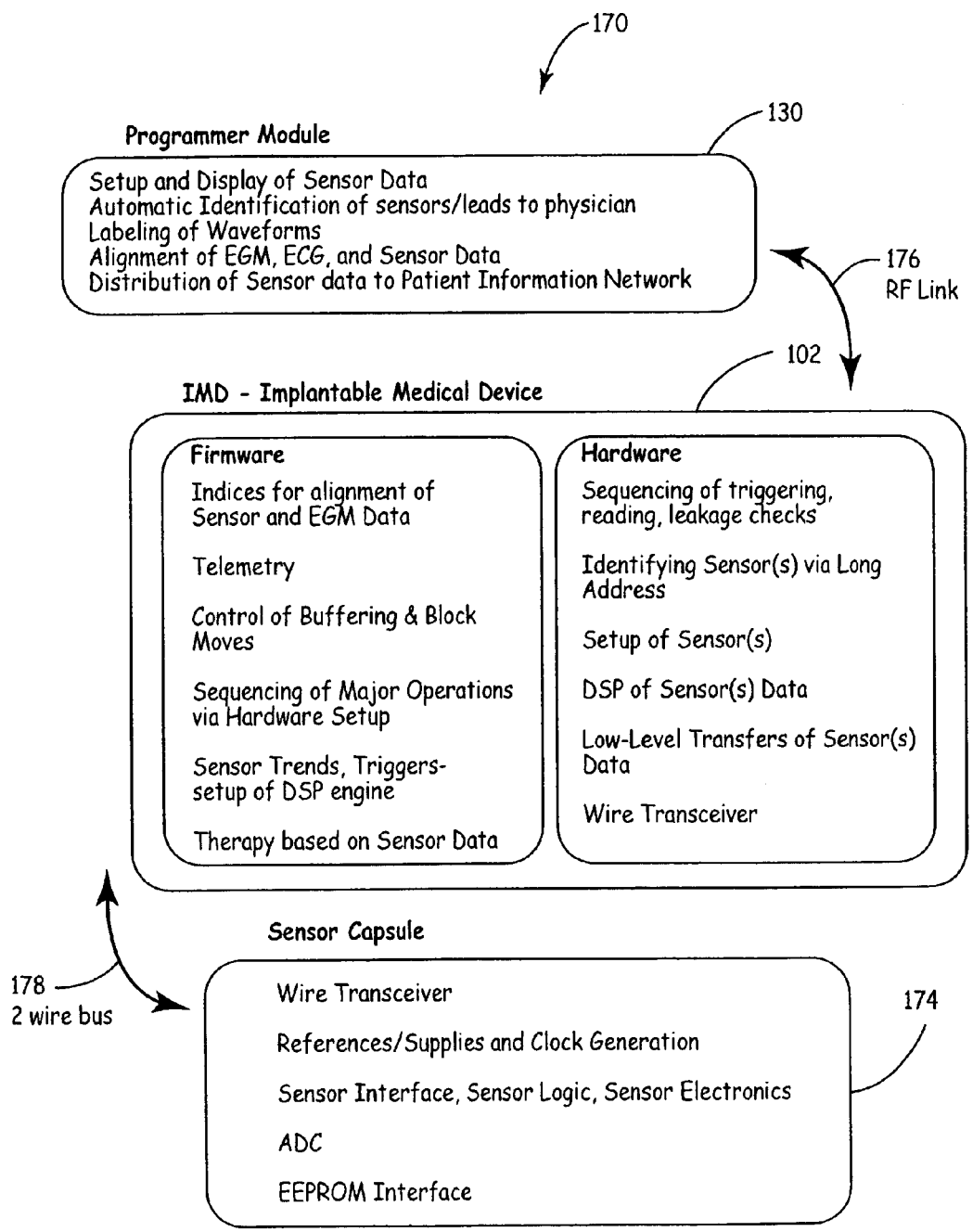
FIG. 3 is a block diagram of an implantable medical device system implementing a sensor communication protocol between a programmer module, an IMD and a sensor capsule.

FIG. 3 is a block diagram of implantable medical device system 170 implementing sensor communication between programmer module 130, IMD 102 and sensor capsule 174. Three communication protocols are defined to move data from sensor capsule 174 to micro-controller 146 within IMD 102. The first protocol defines how sensor data is digitized and moved to a small buffer memory within recovery unit 156 in sensor capsule 174. This protocol also defines how data is read/written from/to an EEPROM within sensor capsule 174 and placed into buffer memory. This protocol is defined by hardware within each sensor capsule.

The second protocol is a sensor communication protocol that defines how data is moved from memory within a transceiver at one end of two-wire bus 178 to memory within a transceiver at the other end of two-wire bus 178. The sensor communication protocol defines an addressing scheme, data encoding, and voltage/current levels on two-wire bus 178. Finally, a third protocol defines how data is moved from a transceiver within IMD 102 to the appropriate locations. Once data is received by IMD 102, it becomes available in memory for signal processing, waveform compression, telemetry, and episode storage. This protocol is defined by hardware and firmware within IMD 102.

The sensor communication protocol defines how data is moved between remote sensors and IMD 102 via two-wire bus 178. Network protocols generally have multiple layers. The sensor communication protocol is therefore described using the open system interconnection ("OSI") model for a network. All layers defined in the OSI model are not necessary for the present invention. The OSI model is broken into 7 layers. The physical layer determines how a bit is moved across the wires (voltage, current, timing). The data link layer determines how frames of data are created (bytes, words). The network layer determines how packets of data are assembled. The transport layer determines how packets are moved. The session layer defines how a session is started and ended. The presentation layer determines how data is compressed or encrypted. The application layer determines how data is used at the highest level. The application layer is defined by the circuits, firmware, RAM-ware, and software running in IMD 102 and/or programmer module 130.

According to an embodiment of the present invention, the physical layer determines how "1's" and "0's" are moved between IMD 102 and sensor capsules 174 via two-wire bus 178. The physical layer also determines how remote sensors are powered from IMD 102. The two-wire bus 178 provides synchronization between sensors 174 and IMD 102. This allows IMD 102 to control when a sensor makes a sample and maintains synchronous operation of all sensors. The physical layer also defines how the integrity of the wires can be checked.

The transmission of power from IMD 102 to remote sensor capsules is provided because the sensors are in some embodiments small enough to pass through the veins and into the heart. That is, certain unpowered sensors may be used that lack as internal power.

Synchronization is important for applications requiring sensors at different locations (e.g. EGM, RA and RV pressure). If each sensor sends data at a slightly different rate, it becomes more difficult for IMD 102 to create records of the sensor data because each sample is taken at a different points in time. Processing of the data also becomes difficult because the time base for the samples is slightly different. For example, calculating a simple difference between RA and RV pressure is complicated if the sample rates are not the same. Data would then be collected at a higher rate from one of the sensors and interpolation or other filtering techniques would be required to time align the sample data. The synchronization signal also allows the clock circuitry within each sensor to be less accurate. If each sensor has to provide data at the same rate without a synchronizing signal, crystal controlled oscillators would be required, which would add significantly to the size of the sensor capsule.

Integrity of two-wire bus 178 is continually verified during operation. Numerous faults could occur on the wires, which could impact the therapy supplied by IMD 102. If the outer insulation of the wires fails in a way that allows current to flow through the heart muscle, the heart could be unintentionally stimulated or fibrillation could be induced. If an insulation fault occurs between the two wires of two-wire bus 178, the battery of IMD 102 could be drained or loaded, thereby causing a loss of longevity or loss of function in IMD 102. If a wire break occurs, a loss in communication with the sensor would likely occur.

EMI filters and/or high voltage protection networks may be optionally installed on IMD 102 and possibly in sensor capsule 174. These networks add capacitance and series impedance, which tend to increase power supply current when driving two-wire bus 178. Furthermore, the use of these networks slows down transitions on the bus and may limit bandwidth.

The wires used to connect the sensors to IMD 102 have characteristics that may limit the performance of the bus in terms of data rate, current drain, and noise immunity. The wire characteristics also affect how signals on the bus couple to adjacent wires on the lead and interfere with these signals. The physical construction of the wires further defines the types of faults in the wires that are most likely to occur and impacts how fault detecting circuitry should operate.

Figure 4:
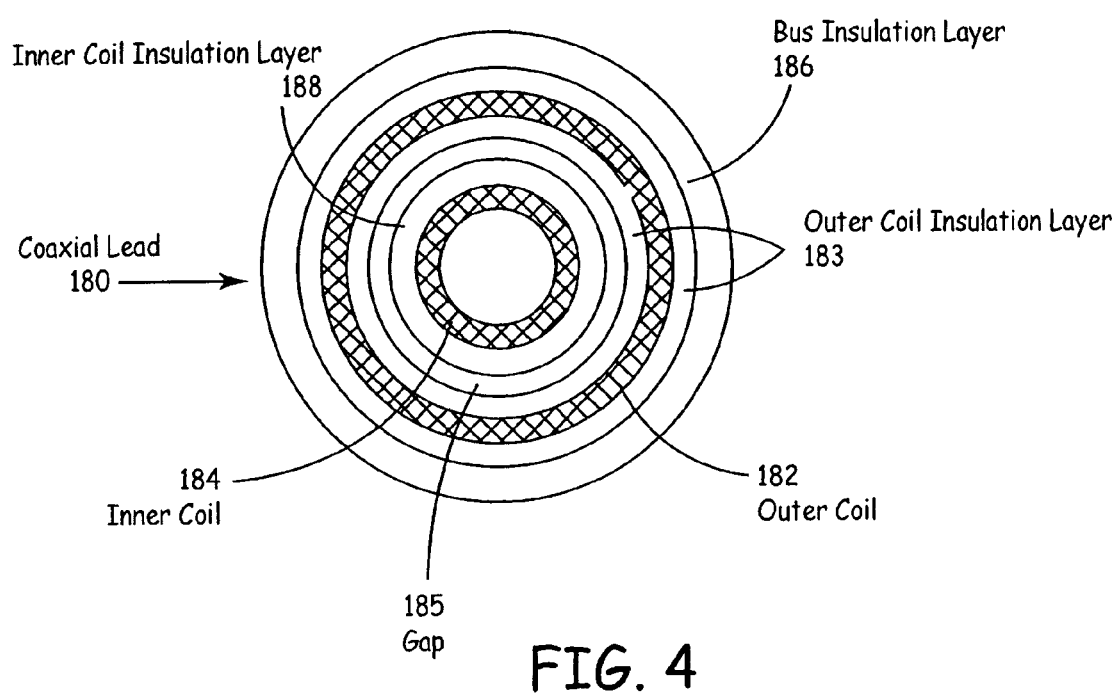
FIG. 4 is a cross section of a co-axial two-wire bus lead.

FIG. 4 is a cross sectional view of a typical two-wire bus lead in the form of co-axial lead 180. Outer coil 182 is connected to the sensor capsule, and to system ground on IMD 102. Inner coil 184 is also connected between a sensor capsule and IMD 102, and is used for communication. A stylet is insertable within inner coil 184 to aid in positioning the sensor at the time of input.

Bus insulation layer 186 surrounds and protects inner coil 184 and outer coil 182. The outer coil is covered by outer coil insulation layer 183 while inner coil 184 is covered by inner coil insulation layer 188. A gap 185 is formed between inner coil insulation layer 188 and outer coil insulation layer 183. Gap 185 may be air if lead 180 is dry or may gradually fill with fluid if lead 180 is wet.

Bus insulation layer 186 and inner coil insulation layer 188 may be made from e.g. polyurethane (Pellathane 80A). Layers 186 and 188 may optionally be made from a biocompatible insulating material including polyurethanes, ETFE, silicone, or polyamides. Insulating materials with low dielectric coefficients are preferred to minimize capacitance between conductors. The gaps between the insulation and conductors will be air when the lead is dry or may gradually fill with water when the lead is wet. Outer coil 182 and inner coil 184 can be made from biocompatible conductive materials including MP35N, platinum, or silver cored MP35N. Conductive materials with low resistance are preferred.

Figure 5:
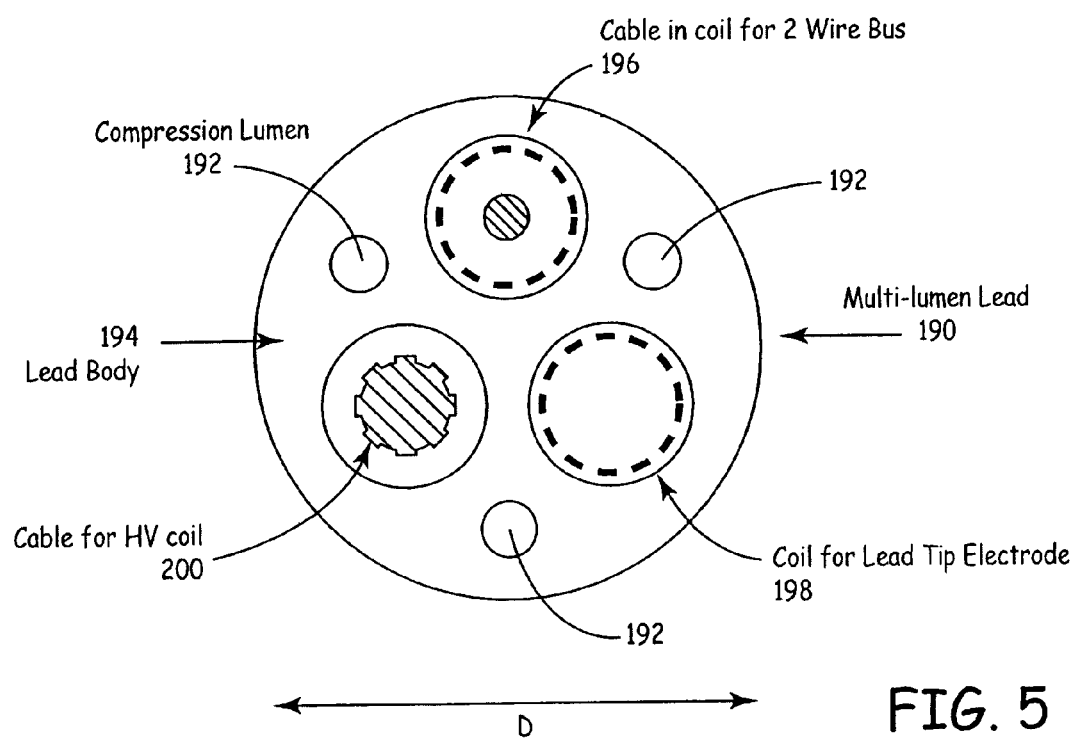
FIG. 5 is a sectional view of a multi-lumen lead.

FIG. 5 is a sectional view of an exemplary multi-lumen lead 190. In particular, multi-lumen lead 190 is a three lumen high voltage lead intended for an implantable cardiodefibrillator ("ICD") and pressure sensing application. Lead 190 supports integrated bipolar sensing, a high voltage RV coil, and uses a coaxial cable for communication with a pressure sensor. Lead 190 includes a plurality of compression lumens 192 defined by lead body 194. Lead 190 uses one cable with a coil 196, one coil 198, and a cable for HV coil 200.

The coil 198 is connected to the tip electrode and is used to allow the stylet to pass through to the tip. The cable within coil 196 is used for sensor communication and is preferably silver cored MP35N with an ETFE insulating layer. Cable 200 is used for a high voltage ("HV") coil. The resistance of the conductors is low (<<5 ohms).

Figure 6:
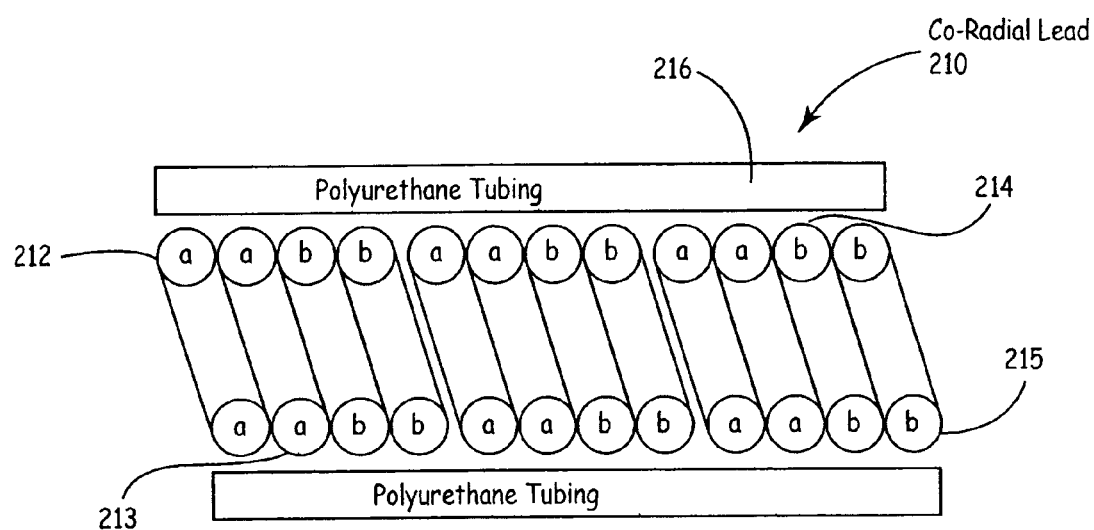
FIG. 6 is an axial view of a two-wire co-radial lead.

FIG. 6 is an axial view of two-wire co-radial lead 210 that uses a co-radial, multi-conductor construction. Lead 210 uses four individual wires wound side by side. Two wires are connected to signal "a" and two wires are connected to signal "b." An outer insulation of polyurethane is used to provide further protection. Wires 212(a), 213(a), 214(b) and 215(b) are wound adjacent to each other rather than one on the outside and one on the inside. The wires are wound together with two wires used for each signal. Polyurethane tubing 216 covers each of wires 212–215.

Figure 7:
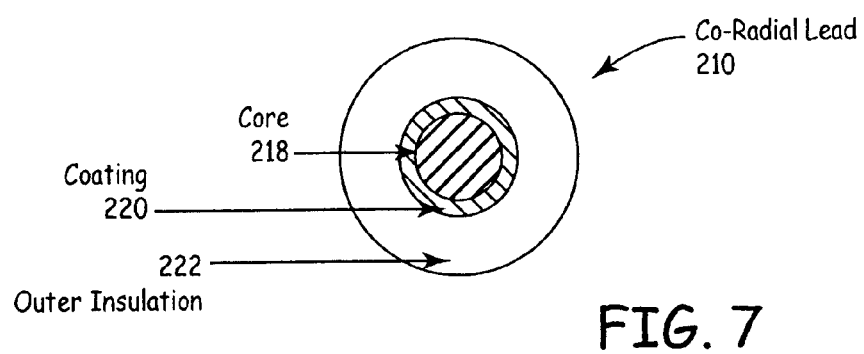
FIG. 7 is a sectional view of an exemplary wire used in a two-wire co-radial lead.

FIG. 7 is a sectional view of the conductors used within the co-radial lead 210, including a core 218. Wire core 218 is dipped in a polyamide coating 220. Each wire 212 is further insulated with outer insulation 222 ETFE.

Figure 8:
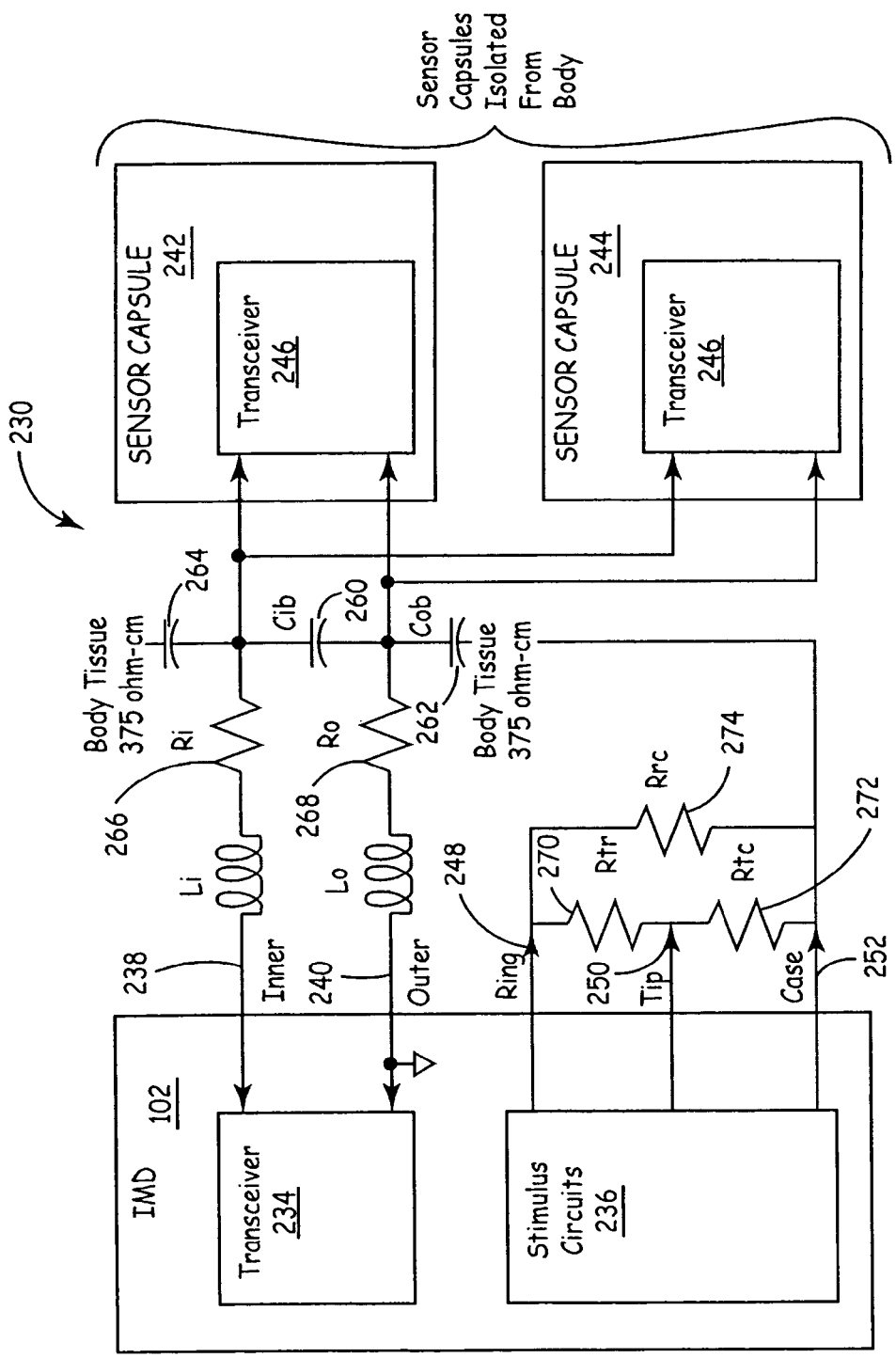
FIG. 8 is an electrical model illustrating electrical interference of sensor leads.

FIG. 8 is an electrical model 230 illustrating electrical interference of sensor leads. Electrical model 230 includes IMD 102, which includes transceiver 234 and stimulus circuits 236. Inner wire 238 and outer wire 240 connect IMD 102 to sensor capsule 242 and sensor capsule 244. Each sensor capsule has an interior transceiver 246. Electrical interference from stimulus circuits 236 to the body tissue are modeled through ring 248, tip 250 and case 252.

There are several variables that affect performance of the communication link, such as signals on the wires coupling into the body causing sensing errors, signals in the body coupling into the wires causing data errors, EMI coupling into the wires causing data errors, CVF current, and effects due to sensors turning on/off. These factors can change by several orders of magnitude depending on the lead parameters, methods used for stimulating tissue and sensing, as well as methods used for EMI and high voltage protection in IMD 102.

In electrical model 230, Cio 260 models the capacitance from inner conductor to outer conductor of the coaxial cable. Cio 260 directly affects current drain of the system because current is proportional to capacitance*voltage*frequency ("CVF"). Cob 262 models the capacitance from outer conductor to the body tissue. Cob 262 directly affects crosstalk from external noise sources into the communication lead and allows communication signals to couple into the body, where they could cause sensing problems in IMD 102. Cib 264 models coupling from the inner conductor of the cable to the body. Normally this will be very low in a coaxial lead configuration because the outer conductor shields the inner conductor from the body. Ri 266 and Ro 268 model the resistance properties of the inner and outer conductors. Ro 268 is especially important for rejecting noise from the body and for preventing crosstalk from the communication protocol to the body. Any voltage change in the body relative to ground results in a current flow in the outer conductor due to Cob 262. This current is converted to a voltage by the resistance of the outer conductor Ro 268.

The tip 250, ring 248, and case 252 of the stimulus/sensing electrodes are modeled as if coupled to the body through resistors. In reality, these electrodes are complex distributed impedances. IMD 102 is shown electrically connected to the lead through the body tissue. Case 252 of IMD 102 is typically the largest electrode in a pacemaker/ICD and is typically the most representative of the voltage seen in the body. In some IMDs, the case is tied to system ground through a low impedance switch, while in others the case is left floating. In this example, Rtr 270 and Rtc 272 are modeled as 830 ohm resistors, while Rrc 274 is modeled as a 415 ohm resistor.

During a bipolar pace sequence, case 252 is left floating, ring electrode 248 is tied to system ground, and tip 250 is driven to a large negative voltage (0 to –9 V). The case voltage ends up somewhere in between the tip and ring voltage, but typically stays closer to ring 248 than tip 250 because the ring electrode area is typically larger than the tip, thereby creating a lower impedance connection. For a unipolar pace, case 252 is held to ground while tip 250 is driven negative. In this scenario, case 252 stays close to ground.

In some pacing systems, the stimulus circuits ground the tip, while pulsing the ring or case positive. In these systems, the case typically moves a greater distance from ground thereby inducing a larger voltage in the body relative to system ground. Depending on the method of implementation for the pacing system, voltage pulses on the case may reach 9 V with respect to system ground. In nerve stimulators, this value can be as high as 15 V. Rise times for the leading edges of pacing pulses are typically on the order of 100 ns-1 us.

Pacemakers and implantable cardiodefibrillators ("ICDs") typically address high voltage protection differently. In an ICD, the case moves as much as 800 V with respect to ground during discharge. Rise times on ICD pulses are typically very fast with slew rates on the order of 500 V/us at the leading edge. During trans thoracic defibrillation, the case moves as much as 1600 V with respect to ground. Rise times on trans thoracic defibrillation pulses are typically much slower than for ICD's.

In a pacemaker, voltage on the leads is clamped with protection networks. This reduces the voltage on the leads as seen by the implantable medical device ("IMD"), but the voltage is still very large in the body. Similar voltages can be seen in the body during electro-surgery. A voltage limiting network may be incorporated within IMD 102 and in the sensors.

Interference into the communication wires can occur if the capacitance on the outer lead conductor is large and the impedance of the outer lead conductor is large. As an example, a large amplitude unipolar pace in a pacemaker uses a pace case architecture with the sensor lead outer conductor grounded. The voltage induced on the lead outer conductor during the pulse rise time is approximately:

$$Vouter \approx \frac{Cob \cdot Vpace\left(\frac{Ro}{2} + Rswitch\right)}{tfall} \quad \text{EQ. 1}$$

In EQ. 1, Cob is the capacitance between outer conductor and body, Vpace is the voltage on the body relative to ground, tfall is the fall time on the leading edge of the pace, Ro is the resistance in series with the outer conductor and is assumed to be distributed, and Rswitch is the value of the switch on IMD 102 used to connect the lead outer conductor to ground (about 10 Ohms). Thus, it can be seen that interference is minimized by reducing Cob, Ro, Rswitch and increasing tfall.

From the above example, the lead conductor capacitance and resistance properties play an important part in rejecting interference from pacing pulses. The high-voltage multi-lumen lead construction has significantly better performance than the co-axial lead or the co-radial designs due to lower resistance and lower capacitance properties. Further, the architecture used for the pacing circuits and the rise time of the stimulus pulses will be important in reducing the amount of crosstalk. Finally, using the co-radial construction lead results in enough coupling from the pacing pulses to the sensor signal to disrupt communications, if the pulses occur when the signal line is not strongly driven.

Just as voltages on the body can be coupled into the wires used for communications, voltage on wires can be coupled into the body causing interference with sensing operation within IMD 102. Three scenarios are set forth below wherein the coupling to the body could be a factor: from lead inner conductor (through Cib), from the lead outer conductor (through Cob) due to the DC current needed to power the sensor, and from lead outer conductor due to transient current flowing in the leads during voltage transitions from communications.

First, coupling from the lead conductor directly to the body is addressed. Any capacitance between the clock/power/data line to the body may cause an attenuated version of the voltage (Vsignal) on the communication lines to be coupled into the body as a common mode signal to tip 250, ring 248, and case 252. A capacitive divider effect will be formed by Cib, Cob, and Cbody to ground.

$$Vbody \approx \frac{Cib \cdot Vsignal}{Cib + Cob + Cbody} \qquad \text{EQ. 2}$$

This coupling is minimized by reducing Cib and minimizing the voltage transitions on the lead used for communications.

Next is considered a situation where a sensor is enabled and the current flowing through the lead outer conductor causes a voltage drop across the conductor, which is then capacitively coupled into the body through the lead outer insulation. The voltage induced on the lead outer conductor is dependent on the sensor current (Isensor) and the impedance in the lead outer conductor (Rswitch+Ro). The voltage is then coupled into the body through Cob.

$$Vouter \approx Isensor \cdot (Ro+Rswitch) \qquad \text{EQ. 3}$$

This coupling is minimized by reducing Cob, Ro, Rswitch, and Isensor. Alternatively, a resistive impedance could be added to the tip, ring, or case to allow the common mode voltage to quickly bleed away.

Last considered is a coupling from the lead outer conductor. In this case, tip 250, ring 248, and case 252 of IMD 102 float relative to circuit ground. Very fast rise time 200 mV communication pulses and, in some embodiments, 3 V power pulses with 100 Ohm source impedance are applied to the lead inner conductor with the lead outer conductor grounded. The resistance of the lead outer conductor plus any switch resistances cause the current through the lead outer conductor to result in a voltage drop. This results in a voltage spike that will quickly bleed away. The peak of the spike is given by:

$$Vouter \approx \frac{\frac{Ro}{2} + Rswitch}{Rsource + \frac{Ri}{2} + \frac{Ro}{2} + Rswitch} \cdot Vsignal \qquad \text{EQ. 4}$$

The magnitude of Vouter is reduced by minimizing Ro, Rswitch and Vsignal, and maximizing Rsource.

The time constant of the decay is given by:

$$Tau \approx \left(\frac{Ro}{2} + Rswitch + Rsource + Rswitch\right) \cdot Cio \qquad \text{EQ. 5}$$

Tau can be minimized by reducing Ro, Rswitch, and Cio.

This voltage is coupled through the capacitance of the lead outer conductor into the body causing a common mode step in voltage on the tip, ring, and case. These glitches appear as common mode spikes on tip, ring, and case electrodes, which are then be filtered by circuits in the IMD. Typically, sense amplifiers have good common mode rejection and high frequency filtering of the input signals. As an example, if a sense amplifier or EGM amplifier had a first order low pass filter at 150 Hz, this results in an attenuation of the glitch amplitude of approximately 10,000×. For coupling through the lead outer conductor, the multi-lumen approach provides the least coupling and the fastest decay time making any filtering more effective as well as reducing the peak amplitude.

The lead properties have an effect on cross-talk from communications taking place on the sensor wires to the signals on the lead. Also, the effect of turning high current sensors on and off can induce voltages in the body large enough to disrupt sense amplifiers or impedance measuring circuits. The cross talk performance of the high voltage multi-lumen lead is better than the co-axial lead or the co-radial construction lead. Crosstalk can be reduced by minimizing the amplitude of the voltages used on the bus and by reducing the rise/fall times of the signals. The addition of capacitance or resistance to the tip, ring, or case to ground can also help significantly.

There are several potential wire faults that can affect safety and reliability of the system. Typical causes of damage to leads include: crushing of the lead, environmental stress cracking, scalpel nicks, and work hardening of the metal or insulation due to many cycles of flexing. These lead failures can cause gaps in the insulation layers resulting in impedance paths between adjacent conductors and/or impedance paths between the conductors and the body. The lead failures can also cause high impedance paths in the wires.

Safety issues for DC bias powered embodiments of the invention include prevention of DC current flow into the body tissue and prevention of inadvertent stimulation of tissue for a scenario where the insulation fails. Another issue is that a lead fault does not cause a high current condition that could cause the battery within the IMD to discharge prematurely. In the presence of a lead fault, the system should not allow a DC leakage path to the body with an average current greater than 100 nA over 1 second or a pulsed current condition in excess of 100 uA for 0.5 ms.

Options for implementing a leakage detection circuit include issuing a command to the sensors to completely power down the sensors on the bus to allow a leakage check between the conductors and the body at normal supply voltages. Another option is to drop the voltage on the bus to a low voltage level (350–400 mV), which can result in a "0" current state for the sensors on the bus. A preferred mode of implementation is to issue a broadcast command to all bus sensors to go to a "0" current state for a period of time long enough to check for leakage. Circuitry in the IMD may then check for faults between each of the conductors or between each of the conductors and the body. Pulse powered embodiments will generally have different requirements because they do not utilize a constant DC bias in the body.

An important possible lead fault concerns failure of the outer insulation. To minimize the impact of this possible fault, the outer conductor should be maintained at the same DC potential as the body. Some IMDs use a positive battery terminal as a body ground while others use a negative terminal as body ground. In this case, the outer conductor of the lead could be driven to either the positive supply voltage or negative supply voltage. However, a rectifier function within each sensor would be required to allow the conductor polarity to be different for different IMDs. If the co-radial construction method is used, and there is a lead outer insulation fault, there is no shield layer to prevent current flow to the body. Thus, the possibility of a lead insulation fault that could cause a DC current flow into the body for DC bias powered embodiments is greater.

Figure 9:
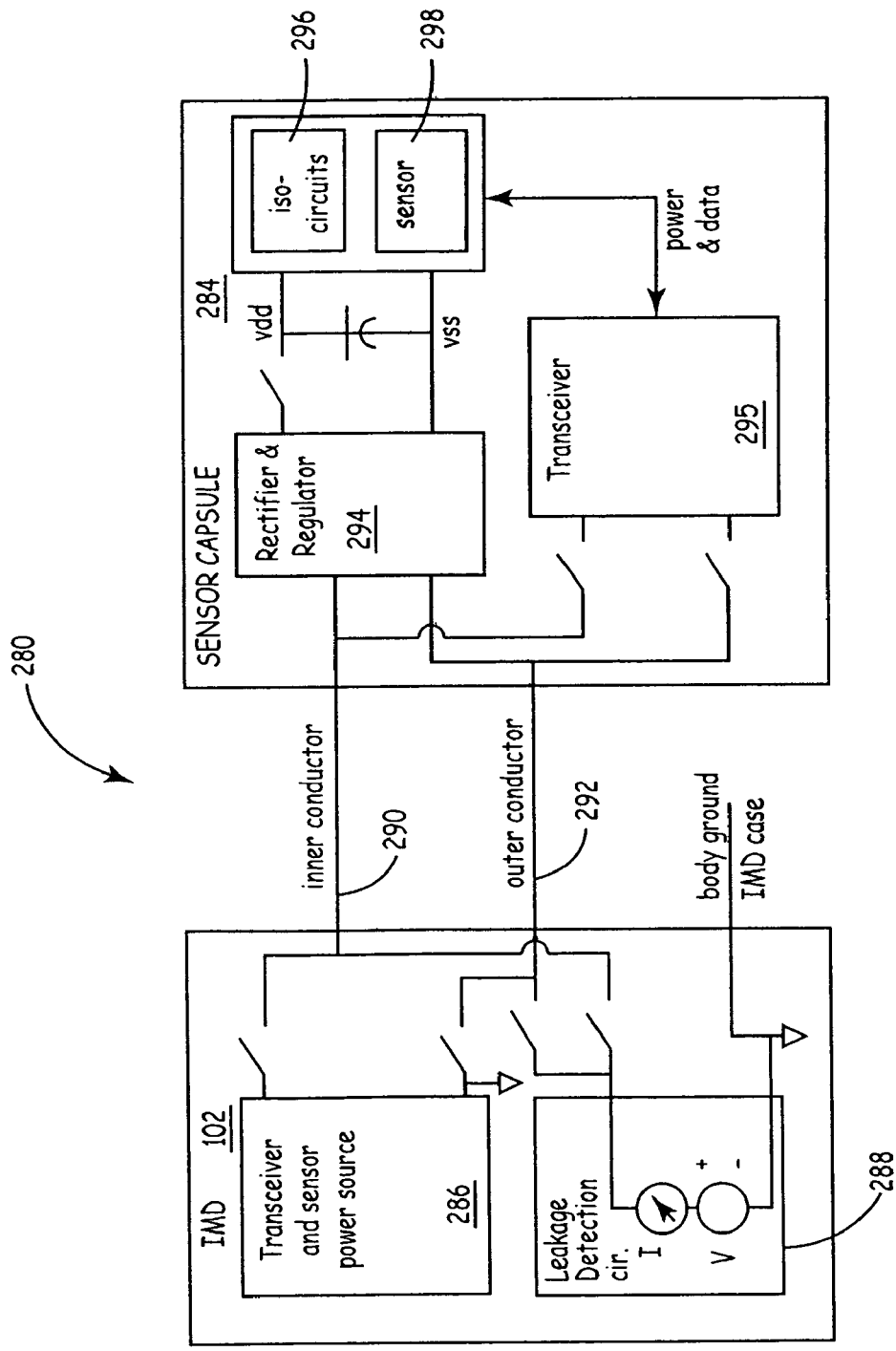
FIG. 9 is a schematic block diagram of a sensor interface system for an implantable medical device and a sensor capsule for lead fault detection.

FIG. 9 is a schematic block diagram of a sensor interface system 280 for an implantable medical device ("IMD") 102 and a sensor capsule 284 for lead fault detection. IMD 102 is capable of switching the transceiver and sensor power source 286 or a leakage detection circuit 288 onto inner conductor 290 or outer conductor 292. The outer conductor 292 of the lead is normally connected to body ground, but can be isolated by a switch. The sensor capsule 284 includes a rectifier & regulator 294 to accept voltages of arbitrary polarity from IMD 102. The sensor capsule 284 includes sensor 298 and also includes isolation circuits 296 for isolating the rectifier and regulator 294 and transceiver 295 from the lead conductors, during a lead integrity check.

Currently developed sensors have differing operating voltage requirements. With multiple sensors on a bus, it is desirable to provide as large a DC bias voltage or voltage pulses as is practical for the supply, and allow each sensor to regulate the required voltage to a required level. In DC bias powered embodiments, this also reduces the effects of line voltage drops due to changing load currents. The maximum voltage level conveniently available in IMD 102 is the unregulated battery voltage, which can be as high as 3.3 V at beginning of life, typically 2.65 V at an elective replacement indicator, and as low as 1.8 to 2.2 V at end of battery life.

Each sensor has a different operating current drain. Most have low operating currents (1–10 uA) and will be turned on for a few milliseconds each second or run continuously. Some sensors, and/or the EEPROMs within the sensors, may require currents in the milliamp range. If the source impedance of the battery, supply circuitry, and wire resistance is high, the milliamp current pulses could disrupt communications in DC bias embodiments. A few methods are available to address this issue, such as formulating a design protocol to operate through the high current pulses or suspending communications during high current measurement. Another method includes storing charge on a capacitor in the high current sensor and to isolate the sensor from the bus. The preferable method is to suspend communications during high current measurement.

A two-wire bus provides power, clock, and data from a single master to up to 16 slave devices. Half-duplex communications, and pulse width modulation of the voltage on the bus allow a raw data rate of approximately 100 Kbps. The "1's" and "0's" are encoded the same for master and slave devices.

An initialization procedure is used to determine the long address of each slave device and to assign a short address to keep the commands shorter. The protocol includes messages to trigger measurements, write, and read data. Addressing modes are provided to allow individual devices, groups of devices, or all devices to be addressed.

For DC bias powered embodiments, the message format includes start, command word, address, data, CRC ACK and stop. In pulsed power embodiments, the message format also includes a Low Power ACK. Some messages require acknowledge by the recipient while others do not. The master device always initiates communications. It is not allowable for a slave device to put data on the bus without the master first requesting the data.

In DC bias embodiments, the start of a message is indicated by, for example, pulling the bus low for 2 bit times nominally. This serves to wake up all slaves such that they are ready to read messages. In pulsed power embodiments, receipt of a power pulse serves to wake up all slaves, and a start sequence following a power pulse indicates the start of a message. Pulsed power embodiments are described in greater detail below with reference to FIGS. 58–60.

Figure 10:
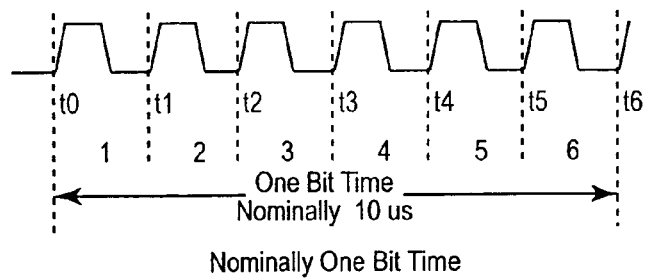
FIG. 10 is graph of one bit time for communication across a two-wire bus wherein the bit time is divided into six equal parts.

FIG. 10 is graph of nominally one bit time for communication across a two-wire bus wherein the bit time is divided into 6 equal parts. One bit time can allow up to an 8% tolerance on the clock in both the sender and receiver.

Figure 11:
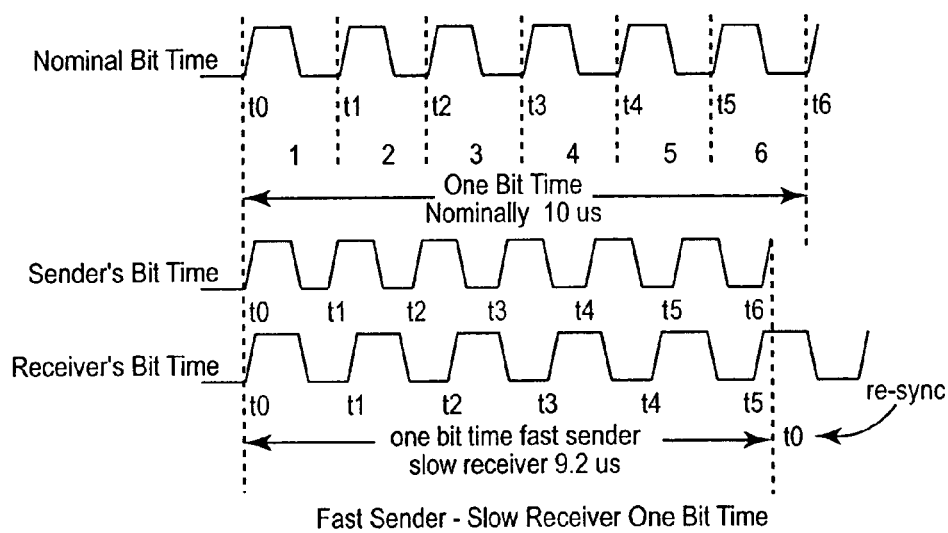
FIG. 11 is a graph illustrating one bit time communication between a fast sender and a slow receiver.

FIG. 11 is a graph illustrating one bit time communication between a fast sender and a slow receiver. In this case, one bit time ends up being 10 us−(0.08×10 us)=9.2 us.

Figure 12:
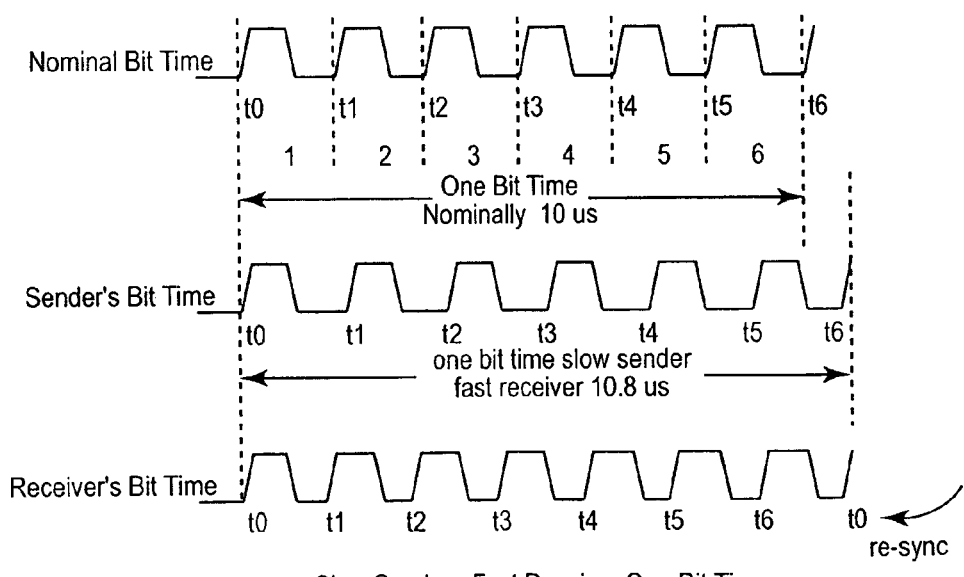
FIG. 12 is a graph illustrating one bit time communication between a slow sender and a fast receiver.

FIG. 12 is a graph illustrating one bit time communication between a slow sender and a fast receiver. In this case, one bit time ends up being 10 us+(0.08×10 us)=10.8 us.

Figure 13:
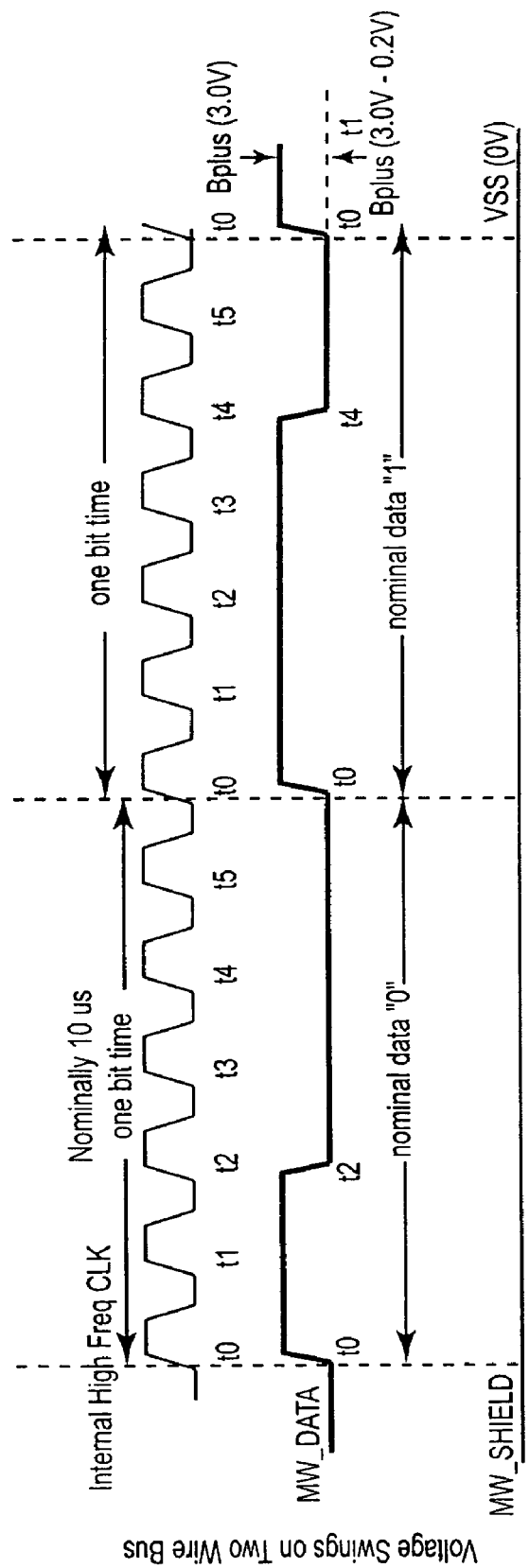
FIG. 13 is a graph illustrating voltage swings on a two-wire bus.

FIG. 13 is a graph illustrating voltage swings on a two-wire bus for DC bias embodiments of the invention. The voltage swings are 200 mV. Signals are driven on the two-wire bus. One wire is labeled "MW_DATA" and is driven between Bplus, e.g., 3.0 V, and Bplus−200 mV. The other wire is labeled "MW_SHEILD."

Figure 14:
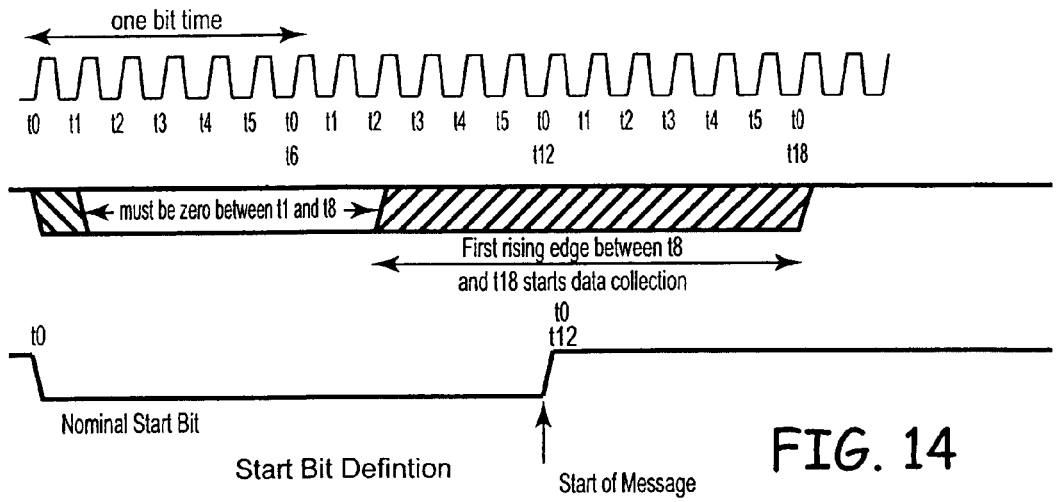
FIG. 14 is a graph illustrating a start bit definition.

FIG. 14 is a graph illustrating an example start bit definition for DC bias embodiments of the invention. The start of a message is nominally a bus low for two bit times, however some variation on clock mismatch is allowed between slave and master so that the slave can wake up and detect the start bit. As will be described in greater detail below, the start bit definition for pulse power embodiments includes three bit times.

The sending of a message from the master to a slave device is first described. The start of a data bit in the message begins with the master pulling the bus up to a high voltage. A fraction of a bit time later, the master pulls the bus back low. The duration of the high voltage pulse indicates the data value.

Figure 15:
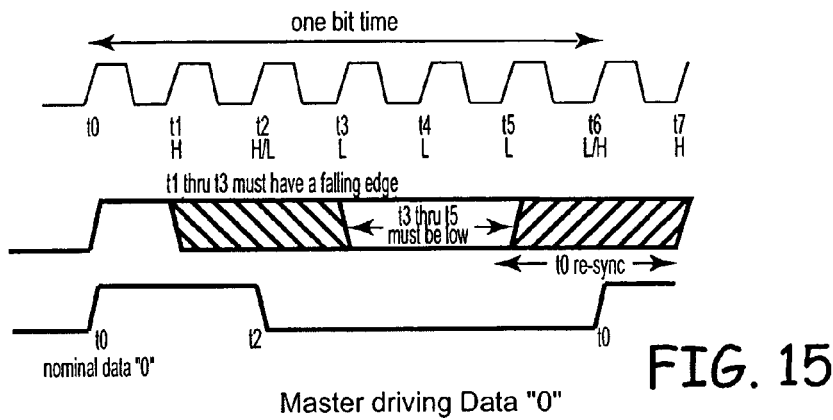
FIG. 15 is a graph illustrating a master driving a data "0"

FIG. 15 is a graph illustrating a master driving a data "0". A data value with a time high of ⅓ bit time corresponds to a logic "0".

Figure 16:
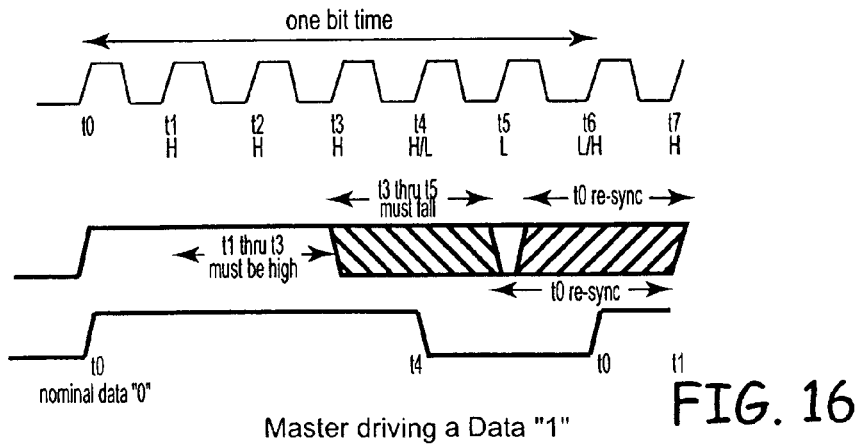
FIG. 16 is a graph illustrating a master driving a data "1"

FIG. 16 is a graph illustrating a master driving a data "1". A data value with a time high of ⅔ bit time corresponds to a logic "1". In its simplest form, the slave's receiver samples the data on the bus with a time delay of ½ bit time (t3) after the rising edge of the bus.

Figure 17:
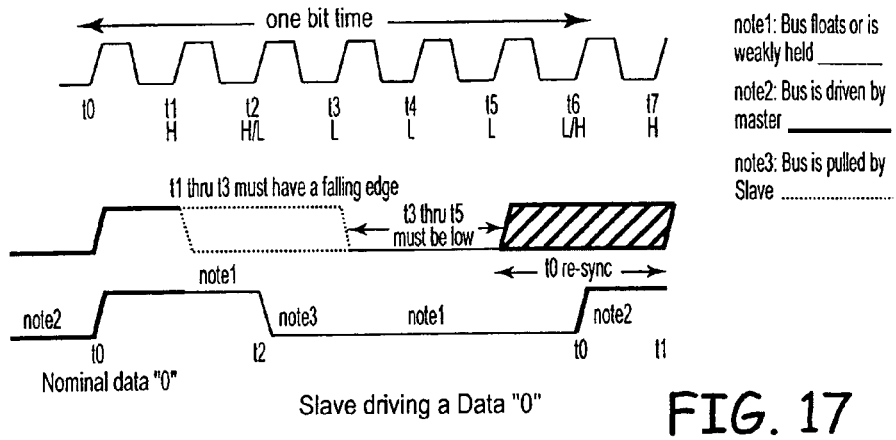
FIG. 17 is a graph illustrating a slave driving a data "0"
Figure 18:
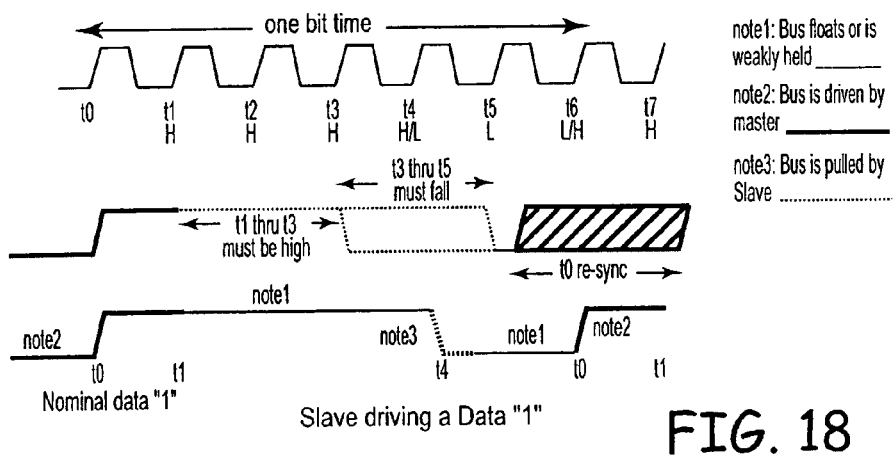
FIG. 18 is a graph illustrating a slave driving a data "1"

FIG. 17 is a graph illustrating a slave driving a data "0", and FIG. 18 is a graph illustrating a slave driving a data "1". The master is the only one on the bus with pull-up capability. At the end of the bit time, the master again pulls the bus high starting a new bit time. When the slave drives data onto the bus, the slave can only pull the bus down. Because the slave cannot pull up, the slave uses timing information to determine whether to send a data "1" or "0". This is essentially the same as when the master is sending "1's" and "0's" but the slave shares driving of the bus with the master.

Figure 19:
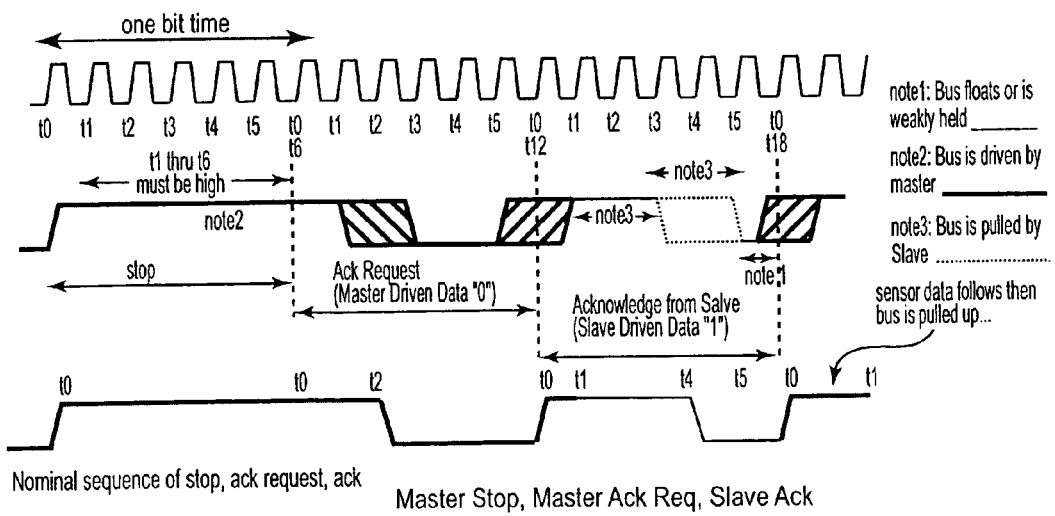
FIG. 19 is a graph illustrating a master stop, a master acknowledge request ("ack req"), and a slave acknowledge ("slave ack")

FIG. 19 is a graph illustrating a stop sequence for DC bias embodiments, which includes a master stop, a master acknowledge request ("ack req"), and a slave acknowledge ("slave ack"). A stop bit is indicated by the bus being held high continuously for 1 bit time. The master can send out commands to multiple slaves. If multiple slaves are responding, then some slaves may be acknowledging the message and others may not. A multi-slave acknowledge therefore is of limited value because if received, the master only knows that at least one slave received the message. The master ends commands with a sequence that the data link layer refers to as Stop-Ack Req-(N)Ack. If the master requires an ACK to the last command, the master will put a logic "0" on the bus in the bit time immediately following the stop bit. If a request for an ACK is given, the slave device will respond with a logic "1" in the next bit time as an indication that the slave received the message. As will be described in greater detail below, the master stop sequence for pulse power embodiments additionally includes a Low Power (N)Ack in addition to the illustrated CRC (N)Ack.

Figure 20:
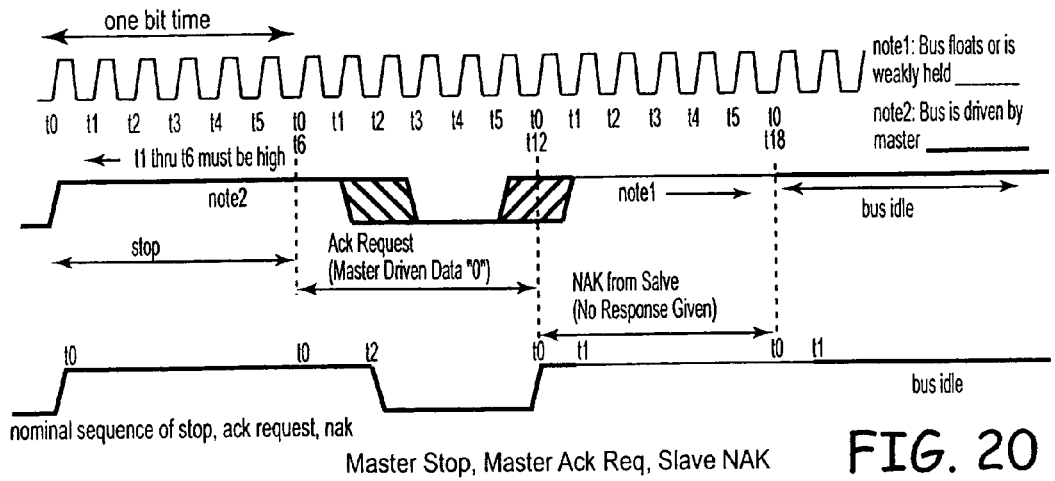
FIG. 20 is a graph illustrating a master stop, a master ack req, and a slave non-acknowledge ("nack")

FIG. 20 is a graph illustrating a master stop, a master ack req, and a slave non-acknowledge ("nack"). If the slave does not receive the message at all, or if the message is received with an error, no ACK or NACK will be provided and the command will be ignored. Defining what is an error based on the command structure and error checking is also further defined in the data link layer.

Figure 21:
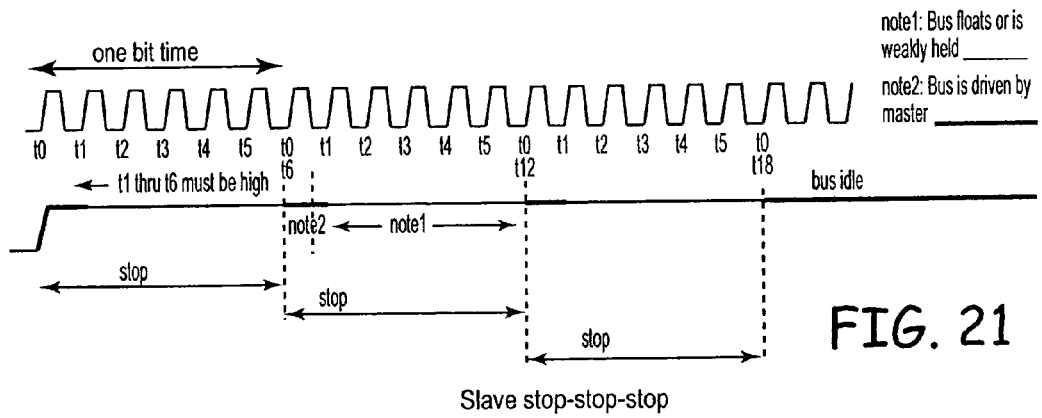
FIG. 21 is a graph illustrating a slave stop-stop-stop.

FIG. 21 is a graph illustrating a slave stop sequence for DC bias embodiments, which includes a stop-stop-stop. When the slave drives data onto the bus in response to a command, the slave drives "1's" and "0's" out to the master. Upon the last bit of data being sent, the master is still unsure if any more data is to follow. Accordingly, the master allows three chances for the slave to send more data. This is referred to as a STOP-STOP-STOP. The stop bit from the slave is indicated by the lack of data on the bus for a period of 1 bit time for a consecutive 3 bit times in a row. The stop sequence occurs for 3 bit times in a row to avoid conflict on the bus where the sensor is pulling down and the master is pulling up at the same time. As will be described in greater detail below, the sensor stop sequence for pulse power embodiments includes four bit times, and takes the form of a STOP-AckReq-(N)Ack-STOP.

Figure 22:
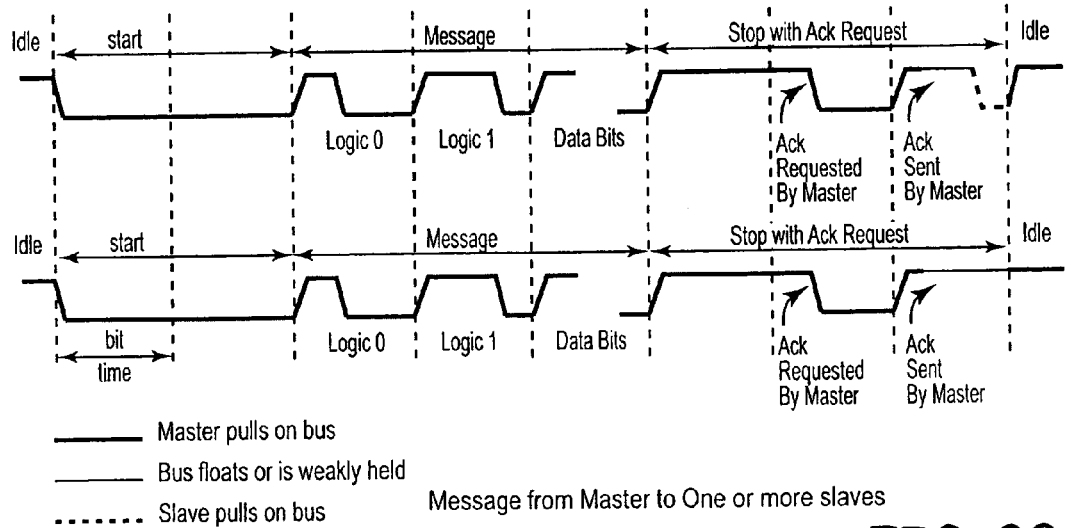
FIG. 22 is a graph illustrating the sending of a message from the master to one or more slaves.

FIG. 22 is graph illustrating the sending of a message from the master to one or more slaves. Thus, a message from the master to one or more slaves is summarized as a start sequence, some data, and a stop sequence.

The slave device uses a delay chain triggered off the rising edge of the bus to determine when to sample the bus voltage. The rising edge of the bus is used to reset the falling edge of the slave's clock low and the ½ bit time delay after the rising edge of the bus is used to set the slave's clock high. The clock is then used to sample the data on the bus and to synchronize the data with the clock.

Figure 23:
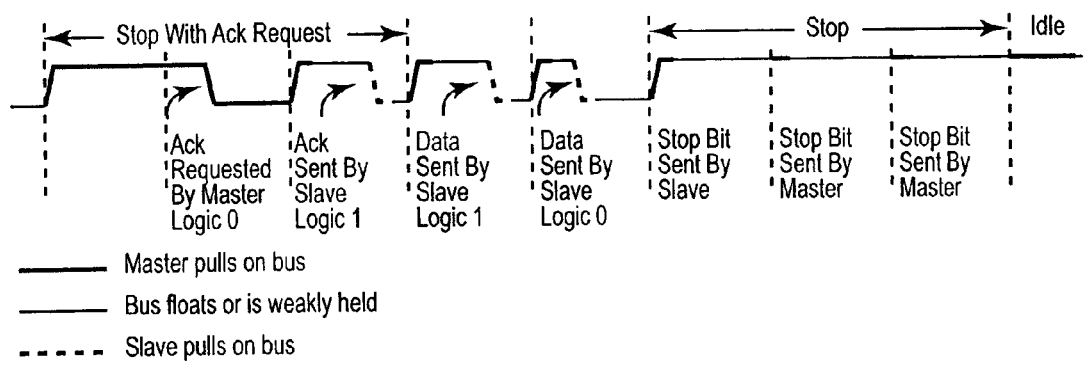
FIG. 23 is graph illustrating a response with data from a slave to the master.

FIG. 23 is graph illustrating a response with data from a slave to master. First, the master requests data from the slave by sending a complete message. All commands that require data from the slave will be preceded by the ACK request. The slave will then put an ACK on the bus and follow up with data. The master then pulls the bus high for ⅙ of a bit time and releases the bus. The slave puts data on the bus in the same manner as the master did when the master was sending data by pulling the bus low. In other words, as discussed above with reference to FIGS. 17 and 18, the duration of the high voltage pulse indicates the data value with a time high of ⅓ bit time corresponding to a logic "0" and a time of ⅔ bit time corresponding to a logic "1". Once the slave has pulled the bus low, the slave releases the bus at t=⅚ of a bit time. The master continues to pull the bus high at the start of each bit time until the master receives a stop bit by the slave indicating the data transmission is complete. When the master recognizes the stop bit from the slave and determines that the message was received correctly, the master finishes the stop command by putting two more stop bits on the bus.

To prevent contention on the bus, the bus master releases the bus before the sensor tries to pull it low. The slave also releases the bus before the master pulls the bus back high. To meet this requirement, the longest value possible for ⅚ of a bit time seen in the sensor must be less than the shortest value possible for 1 bit time as seen by the master. This puts an accuracy tolerance on the time delays of about +/−8% if rise-fall times and propagation delays for detecting clocks and turning on/off pull-ups and pull downs are neglected.

In some embodiments, the master weakly holds the bus high while waiting for the slave to pull the bus down for a data "1" or "0." The master drives the bus high for ⅙ of a bit time at the start of the bit time, and then weakly holds the bus high while waiting for the slave pull the bus low at ⅓ or ⅔ of the bit time for a data "0" or data "1", respectively. Once the bus is pulled low by the slave, the master detects that the bus is in the low state and weakly drives the bus low. When the master detects that the bus is in the low state, the master quickly releases its weak hold high, e.g., within 100 nanoseconds, to minimize power consumption.

The slave releases the drive to the bus that is pulling it low at ⅚ of the bit time, leaving the master weakly holding the bus low. The master disconnects a weak hold switch prior to pulling the bus high for the start of the next bit time. Typically, the strong drive from the master or slave, which is used to pull the bus high or low, will be on the order of 50 Ohms, while the weak hold used by the master to weakly hold the bus high or low will be much higher, e.g., on the order of 5 kOhm, to insure that the slave can overdrive the weak pull up. In embodiments where the master weakly holds the bus high while waiting for the data response from the slave, the communication system operates with less errors in a noisy environment and with lower impedance across the two wires of the bus when the slave is responding to the master than in embodiments where the master allows the bus to float high while waiting for the data response from the slave.

The task of a data link layer is to take a raw transmission facility and transform it into a line that appears free of transmission errors. The data link layer accomplishes this task by breaking up the input data into data frames, transmitting the frames sequentially, and then processing the acknowledgment frames sent back by the receiver. The application layer determines the set of allowed messages and the action taken upon receipt of each.

Data transmission is based on a master-slave relationship. The master initiates all communication by sending commands to the slave, which then responds with actions or data. This allows more hardware intelligence to be placed in the master IMD, which has more resources such as a battery, a crystal oscillator controlled time base, and more area for integrated circuits and external components. The slave electronics are provided to be simple and low in power. The slave may, of course, still support intelligent operations. Signal processing in the slave allows the sending of processed data rather than raw data back to the master, thereby resulting in fewer transferred data bits.

FIG. 24 is a general command format for transferring data across a two-wire bus. Commands are preceded by a Start sequence and all slaves on the bus wake up in response to a Start. The fields are labeled Master1 through Master7, implying that the master is talking. The data is sent out from the most significant bit ("msb") first proceeding to the least significant bit ("lsb").

The field formats are configured as follows. In the illustrated DC bias powered embodiment, the Start field is a unique 2 bit time long sequence issued by the master. The Slave(s) field is a field to identify one slave (unicast) multiple slaves (multicast) or all slaves (broadcast). The Slave(s) field is explained more fully below with regard to addressing. The Quick Trigger ("QT") field is a special field identifying a Quick Trigger ("QT bit set") command. All commands except the Quick Trigger ("QT bit set") have this bit set to zero. When the QT bit is set high, the command is identified as a Quick Trigger command.

The Master Command Name field provides instruction to the slave. A 5 bit command in the Master Command Name field identifies up to 32 different commands. If the QT bit is set, then this field is not used. The Data field is 8 bits long for most commands. The use of 8 bits allows a byte of data to be written at a time. The data field varies from command to command and can be broken down to sub-fields. The frame check sequence ("FCS") field provides error checking. The FCS field is used for a cyclic redundancy check ("CRC").

The Stop Sequence field is used to tell the slave when the master is talking and that this is the end of the command. When the slave is talking, the stop sequence is used to tell the master that this is the end of the data. The stop sequences for DC bias embodiments take two forms discussed above, namely Stop-Ack Req-(N)Ack and Stop-Stop-Stop. In the Stop-Ack Req-(N)Ack form, the talker is asking the listener if they received the message and if the message was error free. "Ack Req" means Acknowledge Request, "Ack" means Acknowledge, and "(N)Ack" means Not Acknowledge. The Stop-Stop-Stop form is slave data response for the Read and Read Results commands. A bit time is a unit of time (clock cycle) for a "1" or "0".

The command format length is 33 bit times for most commands in DC bias embodiments, and 35 bit times for most commands in pulsed power embodiments, discussed in greater detail below, due to the addition of bit times in the Start and Stop sequences. Because most commands are the same length and format, a simpler form of digital electronics is allowed in a capsule (hermetic body) on a lead. Of course, this area is extremely constrained.

The sensor interface allows the slaves to sleep, thereby saving power. The bus can have multiple slaves hanging on it. These slaves may be sensors, actuators or slave IMDs. The command structure is implemented with the Master initiating all communication. When the Master starts talking, the Master issues a Start command. All slaves begin listening on a Start command, or on detection of a power pulse.

A slave not being addressed by the master may stop listening and interpreting the command to save power. When a particular slave determines that a command is not directed to that slave, the slave may go to sleep until the next Start sequence or power pulse. Sleep mode may occur at different points in the command format, depending on whether the sensor is mapped or unmapped. A mapped sensor has an assigned short address and unmapped sensor does not have a short address.

Addressing is provided in two forms: long address, and short address. The long address is 64 bits while the short address in the command is 6 bits. The long address uniquely identifies the slave telling: 1. manufacturer; 2. protocol version; 3. model identifier; 4. unique serial number; 5. manufacturing facility; and 6. slave number (useful for identifying multiple slaves on a single lead). Error checking of the Long Address is performed internally within the sensor via CRC check or other standard checking procedure.

FIG. 25 is a table providing a slave long address format. The long address contains many bits and the current drain of the data communication is governed by i=cvf, where c=capacitance of the bus, v=voltage swing of data communicating on the bus, and f=frequency of the data on the bus. If the 64 bit long address is used for all commands, the frequency of data on the bus would be exceedingly large for an implantable system. The goal is to have a command structure that allows a map assignment of long addresses to short addresses such that the majority of communication is provided by short addresses. The use of a short address containing only 6 bits will lower the cvf current of the bus. The master communicates to the slaves three different ways: 1. Unicast to one sensor; 2 Multicast (Trigger) up to four slaves simultaneously; and 3. Broadcast to all slaves. A broadcast is sent to every sensor on the bus, and there can be up to 16 slaves simultaneously on the bus.

The 6 bit address is provided to trigger, i.e. Multicast, multiple slaves simultaneously. The 6 bit format permits identification of 16 sensors uniquely and permits all short addresses sent to the sensors to be of the same format. The 6 bit format allows some multicast capability and a unique broadcast code.

Figures 26, 27:
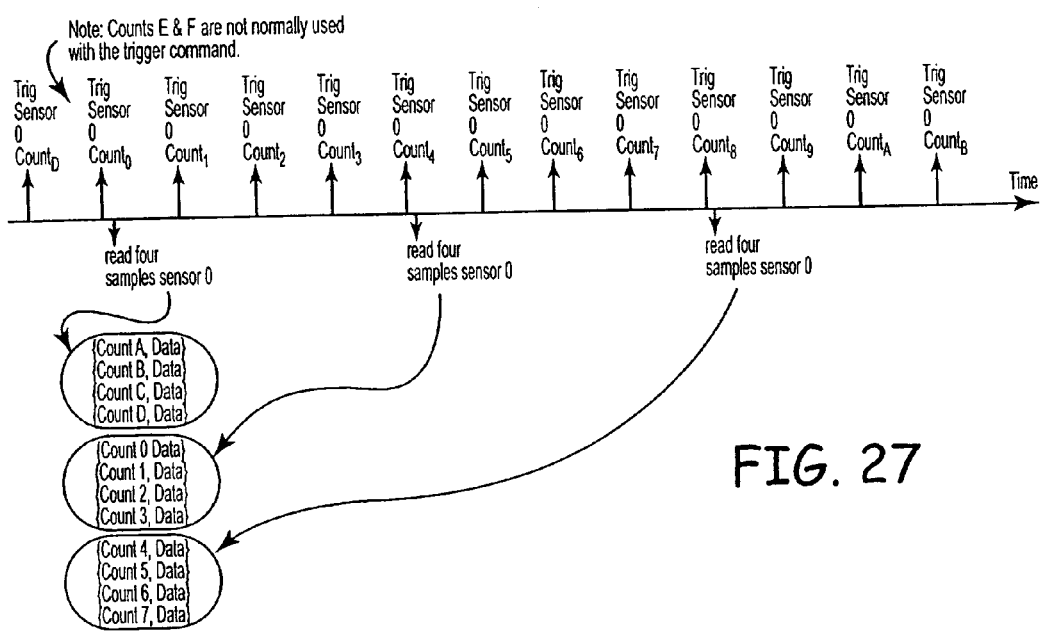
FIG. 26 is a table of slave short addresses and multicast examples.
FIG. 27 is a graph of a triggering example.

FIG. 26 is a table of slave short addresses and multicast examples. The table particularly illustrates examples of how the master specifies the short addresses. According to a preferred embodiment, multicasting a message to more than four slaves is not permitted.

Addressing at power up is particularly considered as follows. Slaves are powered up or reset and respond only to their long address. In this state they are unmapped, and only three commands are usable in this state: 1. Unlocks; 2. Search Long Address; and 3. Write Short Address. These commands can all use a reserved short address with a code of 000000. This reserved code is used as a broadcast command going to all slaves on the bus. When the master uses the broadcast short address of 000000, then all slaves listen. The master may then uniquely identify a particular slave depending on whether the command calls for a long address.

After power up, the long addresses of the slaves are searched. The sequence is as follows: 1. Use the Unlocks command and ensure all slaves are unmapped—forcing all the slaves to be unmapped; 2. Use the Unlocks command and check for any slaves on the bus "check for unmapped" (if a slave on the bus then proceed to next step); 3. Use the Search Long Address and search for the long address of the slave(s) (once all slave long addresses proceed to next step); and 4. Assign each slave a unique short address via the command Write Short Address.

The assignment of long addresses are made during manufacturing. Long addresses may be assigned to various slaves on a pacing lead or to a slave IMD, one slave at a time before each slave is added to the bus. A capsule on a lead is a hermetic body that contains the slave's electronics.

If a capsule contains multiple slaves, the four bit slave number included in the long address can be uniquely hard coded. At capsule test, the master searches the unique long addresses and assign short addresses. The capsule containing multiple slaves then only requires one pair of wires for all slaves. For increased safety, the Unlocks command has a form that "unlocks" the ability to write long addresses. If a lead contains multiple capsules the capsules are assigned unique addresses before they are built into a lead. Each capsule's long address is therefore searched out using the Search Long Address command.

Data going to or from the master contains a Frame Check Sequence ("FCS"). The FCS is an 8 bit CRC. The generator polynomial G(x) is given as follows:

$$G(x)=x^8+x^5+x^4+1 \qquad \text{EQ. 6}$$

Polynomial strings are based upon treating bit strings as representations of polynomials with coefficients of "0" and "1". Therefore, for example, the generator polynomial is the bit string $10011\ 0001_2$.

The master controls when slaves sample by issuing triggers. The issued triggers ensure that all samples are evenly spaced for a particular slave and ensure that all slaves are sampling at the same time or multiples of each other, i.e. data alignment slave to slave. Furthermore, the issued triggers allow the master to control the data rates. The slave's ADC will require a certain amount of time to perform a conversion.

The are two trigger commands: Trigger, and Quick Trigger. The Trigger command allows two additional fields of 4 bits each. One field allows time stamping of data via a Count embedded in the trigger command. This allows the master to tell if a sensor missed a trigger(s) and which trigger(s) were missed. Another field will allow Command Codes to be sent down to the sensor. The sensor may perform signal processing of the data stream between two different Command Codes. Command Codes work like a 4 bit write within the Trigger command.

FIG. 27 is a graph of a triggering example. As illustrated, the read that follows a trigger does not obtain data from the most recent trigger but rather obtains data from 4 triggers previous.

Figure 28:
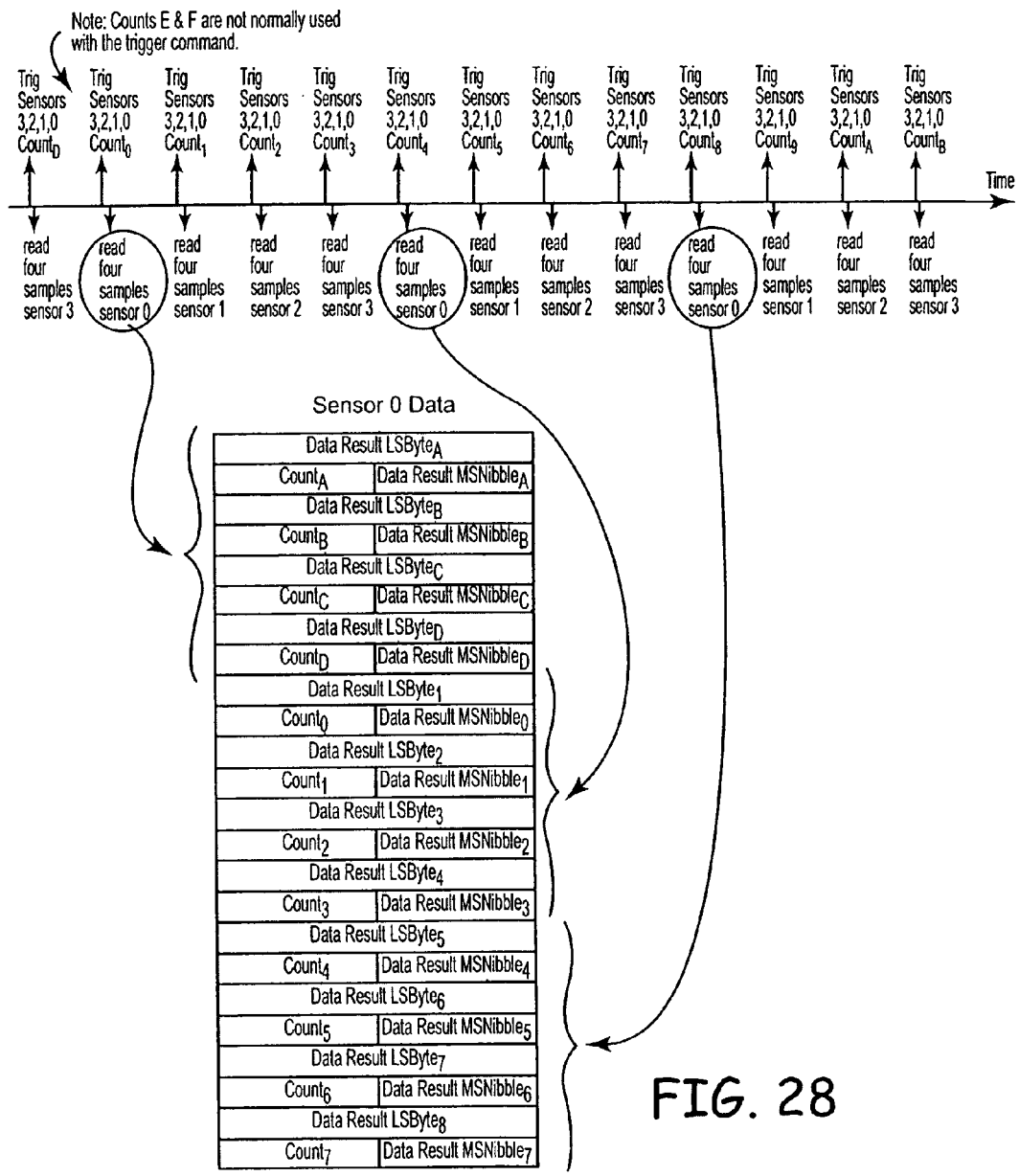
FIG. 28 is a graph and table illustrating a relationship between triggering of one sensor and reading corresponding data.

FIG. 28 is a graph and table illustrating a relationship between triggering of one sensor and reading corresponding data. The graph particularly illustrates an example of triggering four slaves at a same trigger frequency and the staggering of reading the data back to distribute the bus traffic evenly. The Counts that were sent with the triggers are stored in with the data.

The Quick Trigger (QT bit set) works just like the Trigger command, but is less flexible and allows power savings. The Quick Trigger command does not have a Master Command Name and does not have a Command Code. The inclusion of the Quick Trigger command adds a 1 bit overhead to all the other commands but saves 9 bits on the most frequent operation of triggering.

Figure 29:
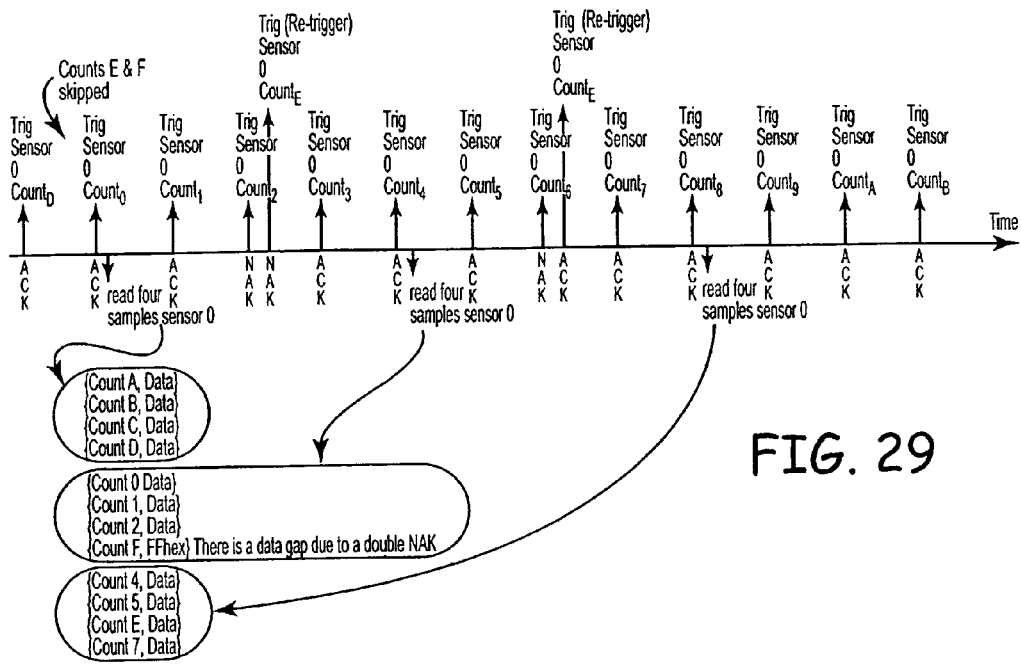
FIG. 29 is a graph illustrating re-triggering of data using a count code.

FIG. 29 is a graph illustrating re-triggering of data using a count code. On occasion, re-triggering of a sample may occur. Re-triggering is a Trigger or a Quick Trigger command with a count code of Ehex. Re-triggering may be used if the slope of the data is not important or is not adversely effected by a re-trigger. Re-triggering may also be used if the sample period is long compared to the time between the trigger and the re-trigger of a sample (implying the slope is not adversely effected). Further, a re-trigger may be used if the data is non-periodic or if only a single sensor is being triggered.

When the trigger is broadcast to multiple sensors, the acknowledge request can be meaningless because more than one sensor is acknowledging proper receipt of the trigger command. When the trigger goes out to a single sensor, the acknowledge has more meaning because the acknowledge is specific to a single sensor. Therefore, if the trigger is NACK'd, the trigger can be determined if re-triggering can be performed. A re-trigger may get ACK'd thereby returning some semblance of periodic triggering.

In pulse power embodiments, triggering can be accomplished by issuing a power pulse to multiple slaves on the bus. Upon receiving the power pulse, the slaves can perform some pre-determined action or measurement. Triggering in this manner reduces bus traffic, thereby lowering current drain.

However, power pulses used as triggers do not include data, such as slave addresses. To selectively trigger a particular slave, the master can deliver a sequence of power pulses that is associated with, e.g., addresses that slave. In such cases, slaves are able to count the number of power pulses issued in order to recognize sequences of power pulses and accordingly perform pre-determined actions.

Some forms of digital signal processing may be performed in the sensor. The signal processing for RV Pressure set forth below may be equally performed in the sensor or in the IMD. If the sensor is area constrained, processing is preferably accomplished in the IMD.

Figure 30:
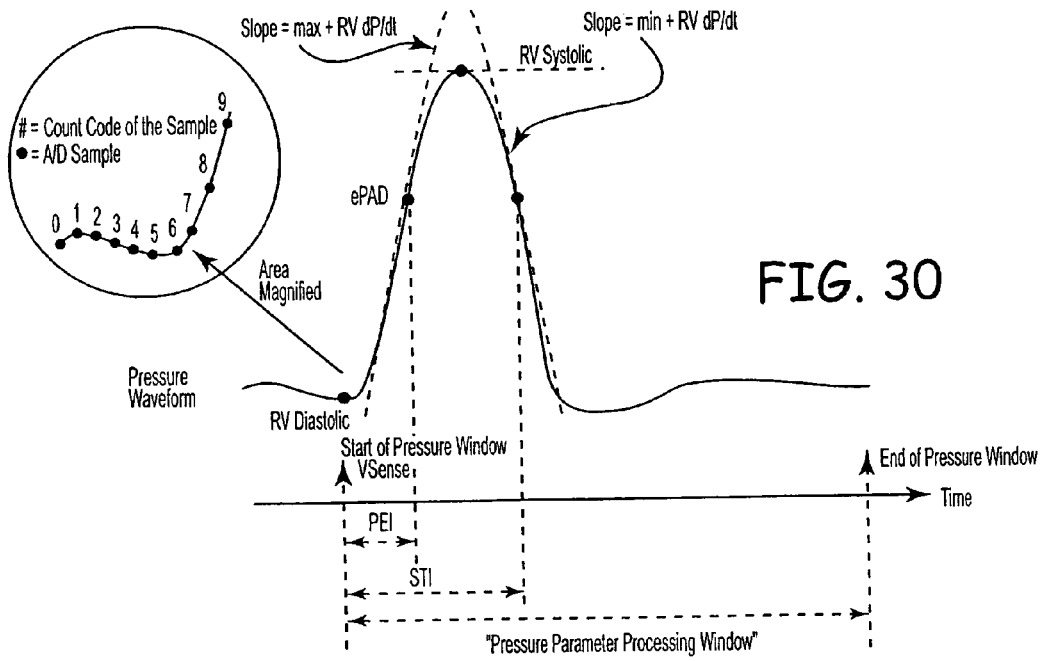
FIG. 30 is a graph illustrating a collection of data points for an RV pressure waveform.

FIG. 30 is a graph illustrating a collection of data points for an RV pressure waveform. FIG. 31 is a table illustrating Command Codes and measured parameters. The advantage of processing in the sensor is to pass only processed information back to the IMD, rather than every waveform point. This lowers the (i=cvf) current drain. The protocol provides for passing the whole pressure waveform up to the IMD for research, diagnostics and display purposes. Commands are sent out by the IMD at a certain rate and each have a 4 bit Count Code associated with them. With these counts, both time and signal slopes can be derived and the presence of missing Triggers can be determined.

The Trigger commands optionally have a 4 bit Command Code associated with them. One use of the Command Codes is to determine when to start the signal processing and when to end the signal processing. The Command Codes are essentially used as a short write command embedded within the Trigger command. As an alternative, the Quick Trigger command in combination with the Write command can be used to start signal processing and end signal processing.

There exists a certain amount of data overhead when retrieving data from the slave. By minimizing the data overhead, the current drain is reduced by reducing the data frequency (f) in the i=cvf equation.

Data transfer overhead for a single slave using a Trigger command and a Read Results command are analyzed below using the 33 Bit Times per standard command for DC bias embodiments as an example. For a one slave application generating 12 bit data and sending 4 bit Count codes back with the data, the following information is obtained.

Each Trigger is associated with 16 bits of data coming back:

$$\frac{33 \text{ Bit Times}}{\text{Trigger}} + \frac{12 \text{ Bits } ADC \text{ Data}}{\text{Trigger}} + \qquad \text{EQ. 7}$$

$$\frac{4 \text{ Bits Count Data}}{\text{Trigger}} = \frac{49 \text{ Bit Times}}{\text{Trigger}}$$

One Read Request and response costs a certain number of bit times:

$$\frac{33 \text{ Bit Times}}{\text{Trigger}} + \frac{8 \text{ Bit Times for } CRC \text{ in Response}}{\text{Read Request}} + \qquad \text{EQ. 8}$$

$$\frac{3 \text{ Bit Times for Stop in Response}}{\text{Read Request}} = \frac{44 \text{ Bit Times}}{\text{Read Request}}$$

Given n triggers to get n samples per Read Request:

$$\frac{n \text{ samples}}{\text{Read Request}} \qquad \text{EQ. 9}$$

For calculation of the number of bit times each sample associated with a trigger costs for a one slave application.

$$\frac{49 \text{ Bit Times}}{\text{Trigger}} + \frac{\left(\frac{44 \text{ Bit Times}}{\text{Read Request}}\right)}{\left(\frac{n \text{ samples}}{\text{Read Request}}\right)} = \frac{X \text{ Bit Times}}{\text{Sample Trigger}} \qquad \text{EQ. 10}$$

If n=4 then we get:

$$\frac{49 \text{ Bit Times}}{\text{Trigger}} + \frac{\left(\frac{44 \text{ Bit Times}}{\text{Read Request}}\right)}{\left(\frac{4 \text{ samples}}{\text{Read Request}}\right)} = \frac{60 \text{ Bit Times}}{\text{Sample Trigger}} \qquad \text{EQ. 11}$$

As set forth below, the efficiency for one slave is not nearly as great as for multiple slaves. In particular, use of multiple slaves using a Trigger and Read Results command provides increased efficiency. Generalized for a quantity of Y slave applications, each slave generating 12 bits data and transmitting a 4 bit Count up, savings are achieved.

Each Trigger command is associated with a certain amount of data (16 bits X the quantity of slaves Y) coming back:

$$\frac{33 \text{ Bit Times}}{\text{Trigger}} + \qquad \text{EQ. 12}$$
$$\left(\frac{12 \text{ Bits ADC Data}}{\text{Trigger}} + \frac{4 \text{ Bits Count Data}}{\text{Trigger}}\right)\frac{Y \text{ sensors}}{\text{Trigger}} =$$
$$\frac{33 \text{ Bit Times}}{\text{Trigger}} + \frac{16 \text{ Bit Times of Data}}{\text{Trigger}} \times \frac{Y \text{ sensors}}{\text{Trigger}}$$

Each slave has its own read request and response that has a certain cost:

$$\frac{33 \text{ Bit Times in Request}}{\text{Read Request}} + \qquad \text{EQ. 13}$$
$$\frac{8 \text{ Bit Times for CRC in Request}}{\text{Read Request}} +$$
$$\frac{3 \text{ Bit Times for Stop in Response}}{\text{Read Request}} = \frac{44 \text{ Bit Times}}{\text{Read Request}}$$

Given triggers to get n samples per Read Request:

$$\frac{n \text{ samples}}{\text{Read Request}} \qquad \text{EQ. 14}$$

The number of bit times each sample costs for a quantity of Y slave application is next calculated:

$$\frac{33 \text{ Bit Times}}{\text{Trigger}} + \frac{Y \text{ sensors}}{\text{Trigger}} \times \qquad \text{EQ. 15}$$
$$\left(\frac{\left(\frac{44 \text{ Bit Times}}{\text{Read Request}}\right)}{\left(\frac{n \text{ samples}}{\text{Read Request}}\right)} + \frac{16 \text{ Bit Times of Data}}{\text{Trigger}}\right) =$$
$$\frac{X \text{ Bit Times}}{\text{Sample Trigger}}$$

If n=4 and Y=4 as in FIG. 28, then:

$$\frac{33 \text{ Bit Times}}{\text{Trigger}} + \frac{4 \text{ sensors}}{\text{Trigger}} \times \qquad \text{EQ. 16}$$
$$\left(\frac{\left(\frac{44 \text{ Bit Times}}{\text{Read Request}}\right)}{\left(\frac{4 \text{ samples}}{\text{Read Request}}\right)} + \frac{16 \text{ Bit Times of Data}}{\text{Trigger}}\right) =$$
$$\frac{141 \text{ Bit Times}}{\text{Sample Trigger}}$$

For 1 trigger resulting in 1 sample for 4 slaves, an average of 32.5 bit times per slave is achieved.

$$\frac{141 \text{ Bit Times}}{\text{Sample Trigger}} \times \frac{1 \text{ Sample Trigger}}{4 \text{ Sensor}} = \frac{35.25 \text{ Bit Times}}{\text{Sensor}} \qquad \text{EQ. 17}$$

Accordingly, 35.25 bit times per slave are produced. Considering the acquisition of 12 bits of ADC data and 4 bits of Count data for time alignment or a total of 16 bits, then a factor of approximately 2× for the protocol is efficient. Moreover, efficiency is further increased by reading larger amounts of data, i.e. by increasing "n" in EQ. 14. The cost of reading more data per read command is a lowered specificity to detect errors in the data.

Using the Quick Trigger command along with the Read Results command also provides increased efficiency as set forth below. Generalized for a quantity of Y slave applications, with each slave generating 12 bits of data and transmitting a 4 bit Count up, efficiency is improved. Each Quick Trigger command is associated with a certain amount of data (16 bits X the quantity of slaves Y) coming back:

$$\frac{24 \text{ Bit Times}}{\text{Trigger}} + \qquad \text{EQ. 18}$$
$$\left(\frac{12 \text{ Bits ADC Data}}{\text{Trigger}} + \frac{4 \text{ Bits Count Data}}{\text{Trigger}}\right)\frac{Y \text{ sensors}}{\text{Trigger}} =$$
$$\frac{24 \text{ Bit Times}}{\text{Trigger}} + \frac{16 \text{ Bit Times of Data}}{\text{Trigger}} \times \frac{Y \text{ sensors}}{\text{Trigger}}$$

Each slave has its own read request and response that has a certain cost:

$$\frac{33 \text{ Bit Times}}{\text{Read Request}} + \frac{8 \text{ Bit Times for CRC in Response}}{\text{Read Request}} + \frac{3 \text{ Bit Times for Stop in Response}}{\text{Read Request}} = \frac{44 \text{ Bit Times}}{\text{Read Request}} \quad \text{EQ. 19}$$

Given Y triggers to get n samples per Read Request:

$$\frac{n \text{ samples}}{\text{Read Request}} \quad \text{EQ. 20}$$

Therefore, the number of bit times each sample costs for a quantity of Y slave application is:

$$\frac{24 \text{ Bit Times}}{\text{Trigger}} + \frac{Y \text{ sensors}}{\text{Trigger}} \times \left( \frac{\left(\frac{44 \text{ Bit Times}}{\text{Read Request}}\right)}{\left(\frac{n \text{ samples}}{\text{Read Request}}\right)} + \frac{16 \text{ Bit Times of Data}}{\text{Trigger}} \right) = \frac{X \text{ Bit Times}}{\text{Sample Trigger}} \quad \text{EQ. 21}$$

If n=4 and Y=4 as in FIG. 28, then:

$$\frac{22 \text{ Bit Times}}{\text{Trigger}} + \frac{4 \text{ sensors}}{\text{Trigger}} \times \left( \frac{\left(\frac{44 \text{ Bit Times}}{\text{Read Request}}\right)}{\left(\frac{4 \text{ samples}}{\text{Read Request}}\right)} + \frac{16 \text{ Bit Times of Data}}{\text{Trigger}} \right) = \frac{132 \text{ Bit Times}}{\text{Sample Trigger}} \quad \text{EQ. 22}$$

For 1 trigger resulting in 1 sample for 4 slaves, then this averages to 33 bit times per slave.

$$\frac{132 \text{ Bit Times}}{\text{Sample Trigger}} \times \frac{1 \text{ Sample Trigger}}{4 \text{ Sensors}} = \frac{33 \text{ Bit Times}}{\text{Sensor}} \quad \text{EQ. 23}$$

Therefore, approximately 33 bit times are required per slave. Considering 12 bits of ADC data and 4 bits of Count data for time alignment or a total of 16 bits, then a factor of approximately 2× for the protocol is efficient. Moreover, efficiency is further increased by reading larger amounts of data, thereby increasing n in the above EQ. 20. The cost of reading more data per read command is a lowered specificity to detect errors in the data.

For a calculation of EQ. 21 for one sensor read every 4 triggers, a value of 51 bit times per sample trigger is determined. Thus, the Quick Trigger command has an efficiency over the Trigger command, which comes out to 60 bit times per sample trigger in EQ. 11.

FIG. 32 is a table providing a command overview for the sensor interface for an implantable medical device. In general, a unicast command writes to a single slave, a multi-cast command writes to more than one slave, and a broadcast command writes to all slaves.

Memory inside the slave is partitioned to hold Calibration Constants, Slave Long Addresses, Lead Long Addresses and other variables to control the operation of the device. The memory is preferably non-volatile for Calibration Constants and Addresses so that data is not lost once the bus is powered down. Memory partitioning is specific to each slave and 16 bit addressing is allowed for both EEPROM and internal RAM/Register memory. Examples of commands using this type of memory are given by: 1. LSB RAM/REG Address; 2. MSG RAM/REG Address; 3. LSB EEPROM Address; 4. MSB EEPROM Address; 5. Copy RAM/REG to EEPROM memory; and 6. Copy EEPROM to RAM/REG memory. Data link layer commands are particularly set forth below for a sensor interface for an implantable medical device.

FIG. 33 is a table illustrating a format for the Unlocks command. FIG. 34 is a table illustrating Unlock command key options. The Unlocks command is used for multiple operations and globally unmaps all slaves. When a slave is unmapped, the slave only responds to its associated long address. The Unlocks command may be sent multiple times because more than one slave is responding and ACKing. Globally, the Unlocks command checks for any unmapped slaves, and is shown as three steps in FIG. 49 below. The Unlocks command also globally checks for any mapped slave, and checks if the Unmap-all command was successfully completed. The Unlocks command allows for copying from RAM/REG address space to EEPROM, and allows copying from EEPROM address space to RAM/REG space. Further, the Unlocks command allows writing of a slave long address. For a command response, the command is either ACK or NACK. The ACK normally indicates that the FCS was valid but if searching for an Unmapped slave, an ACK will only be provided if the FCS is valid and unmapped.

FIG. 35 is a table of a Master's Search Long Address command. With this command, a binary search for the long address can occur. This search occurs with progressively-longer Long Address Bit Patterns (field Master4). If one or more slaves exist at the long address, then the command pulls the line low via the ACK command. Only unmapped slaves respond to this command.

FIG. 36 is table summarizing an example search across a sensor for an implantable medical device. The search is performed by the Master implantable medical device for the binary long address bit pattern of the sensors attached to it. If the long address given below is only 4 bits, two slaves are on the bus at addresses ($1010_2$ and $1001_2$), and the search will progress as illustrated. However, slaves having 4 bit addresses is illustrated for example purposes only.

FIG. 37 is a table illustrating a Master's Write Short Address command. This command writes the short address of a single slave. The Master's Write Short Address Command is given the long address (indicated by the Master4 field) and then a short address defined by the Master2 field is assigned. If the long address matches the slave's long address, then this command marks the short address as mapped. For a command response, the slave will acknowledge the write as long as the FCS is correct. Action will only be taken if the Slave field (Master 2) is Unicast.

FIG. 38 is a table illustrating a Trigger command. The slave to be triggered depends on the Slave(s) field Master2. The sampling rate depends on the speed that the Trigger command is sent by the master, the frequency of Master and Sensor time bases, and the length of the trigger command. If the Trigger command is sent at 250 Hz, the Trigger command could trigger an RV pressure slave to sample every 4 ms.

The Command code for the Trigger command is a 4 bit code that encodes information, i.e. events, such that the slave can associate samples with cardiac or other information. Not all slaves will use the Command code field. Some slaves will use the Command code only and some will use the Command code and the Count and some may use neither the Command code or Count.

Although described herein primarily as sensors, slave devices can take the form of a variety of types of devices in various embodiments of the invention. For example, in some embodiments of the invention slave devices may be other implantable medical devices or actuators. An actuator can take the form of, for example, a miniature drug pump, stimulation device, or a micro-electro-mechanical-sensor device. The master device can trigger sensing or delivery of therapy, opening of a particular orifice for delivery of drugs or selection of a combination of electrodes for delivery stimulation by an IMD or actuator slave, or some other pre-determined action by an IMD or actuator slave. In some embodiments, actuators take the form of sonomicrometry transducers, and the master triggers one or more actuators to act as either transmitters or receivers for one or more measurements. FIG. 39 is a table illustrating a Trigger Command Code for a cardiac IMD. The illustrated list is used to communicate cardiac Command Codes to multiple slaves.

FIG. 40 is a table illustrating an example of a Trigger Command Code for sonomicrometry transmitters and receivers. The illustrated list is used to determine which slave/actuator is making an acoustic ping and which slave/sensor is listening. The Command Code of $F_{16}$ ($1111_2$) is a reserved code for cleared data. The Command Code of $E_{16}$ ($1110_2$) is a reserved code for normal (not specific Command Code data). Accordingly, a code other than $F_{16}$ is allowed to be embedded with most of the samples in case the Command Code is sent back with the Data.

The Count field in FIG. 38 is a 4 bit code that gives a sequence to the triggers that are coming. The Count rotates (in hexadecimal) 0,1,2,3,4,5,6,7,8,9,A,B,C,D,0,1,2,3 . . . The Counts of $E_{16}$ and $F_{16}$ are reserved. The Count of $F_{16}$ ($1111_2$) is a reserved count code for cleared data and the Count of $E_{16}$ ($1110_2$) is a reserved count code for retriggering of a sample that is NACK'd A Slave can determine if a trigger was missed. If sampling on every Count, then the Count should increment $0_{16}$ thru $D_{16}$, if the triggers are emitted to the slave in that order. Time alignment of data between slaves is accomplished in the master. A slave can be told to down sample on even values or odd values of the Count field via the Short Address Field. The Trigger command's Short Address field: $G_1G_0A_3A_2A_1A_0$ still tells the slave to sample or not, therefore the Count does not dictate if a sample occurs. The Count embedded for this slave's data when read via the Read Results command tells whether any data is missing. Sampling on even Counts have Counts embedded in the data such as 0, 2, 4, 6, 8, A, C, 0, 2. Sampling on odd Counts would Counts embedded in the data such as 0, 3, 6, 9, C, 1, 4, 7, A, D, 2, 5, 8, B, 0, 3. The pattern for odd Counts takes longer to repeat itself.

Using Counts for signal processing in the slave are performed and slopes can be calculated, even with missing triggers, because the Count value is given for each trigger. Using Counts and Command Codes for signal processing and time measurements is also utilized. For example, the Pre-ejection interval ("PEI") may be recorded as the time from R wave detection to peak dP/dt. If one of the samples is not one of the reserved Command Code codes: ($1111_2$ or $1110_2$) there could be a code for R-wave detection (for example $0000_2$). Signal processing is performed to pick off the dP/dt via the Count codes. Once the speed of Count increments is determined, the PEI may be recorded as the number of Count increments between when the R wave is signaled and when the pressure slave showed a max +dP/dt.

Not all slaves will use the Count field. Some will use Count only and some will use the Command Code and the Count. Some may use neither the Command Code or the Count. A slave can embed both a Count and Command Code within a data response. Signal processing is performed on the Master end.

For the Command response, an Acknowledge from one or more slaves is provided. The AckReq gives an edge that allows accurate timing for sonomicrometry operation.

FIG. 41 is a table illustrating a Quick Trigger Command. The Quick Trigger works like the Trigger command but uses fewer bits to save power. The Slave(s) field Master2, determines which slaves are triggered. The sampling rate depends on the speed that the Quick Trigger command is sent by the master. For example, if the Quick Trigger command is transmitted at 250 Hz, an RV pressure slave may be triggered to sample every 4 ms. The Quick Trigger command is the only one with the QT bit set.

The Quick Trigger command does not have a Master Command Name Field, therefore the slave must recognize whether the QT bit is set and know that it is the Quick Trigger command. The count field works the same in the Quick Trigger command as in the Trigger command. The count cycles 0 thru D, 0 thru D etc. . . with count codes E and F being reserved. A command response is an Acknowledge from one or more slaves. The AckReq gives an edge that improves timing for sonomicrometry operation.

FIG. 42 is a table illustrating a Master's Read command. The Address for the read is set up via the Master's LSB RAM/REG Address Command and the Master's MSB RAM/REG Address command. The Quantity of bytes field allows reading up to 256 values from a page. A value of "0" reads 1 byte of data.

FIG. 43 is a table illustrating a Slave's Read Response. The Read command will leave the address as set by the Master's LSB RAM/REG Address Command and the Master's MSB RAM/REG Address Command, where it pointed to for the first byte read. For a command response, the slave will acknowledge the read as long as the FCS from the master was correct. A response will be given if the command is Unicast to one slave. The response indicated is a response to reading N-1 bytes.

FIG. 44 is a table providing rules for a Read Results command. FIG. 45 is a pair of tables illustrating a buffer with 8 bit Data and Count and Command Code embedded. FIG. 46 is a table illustrating a Master's Read Results command. The Master's Read Results command is more useful/specific than the general Read command because it performs more for the master, reduces bus traffic and reduces power. The Read Results command reads result data from RAM/Register Address space, and is used in conjunction with slave results being put into this memory typically by an ADC. Data can be put into memory via any format and can be slave specific. As illustrated in FIG. 44, the data format is shown with the oldest data given first.

The Read Results command works in close association with the Trigger and the Quick Trigger commands. The Trigger command forwards a Command Code and a Count that are values other than $F_{16}$. Command Codes and/or Count codes that are embedded in the data read by the Read Results command, and that have values of $F_{16}$, have not yet had ADC data written to their associated data fields. The Quick Trigger works like the Trigger except that it only sends the Count code.

The Read Results command follows the rules given in the table of FIG. 44. The read command is setup to read from a specific buffer (either "0" or "1") and depending on which buffer is being read and which buffer the ADC pointer is pointing to the appropriate set of rules are followed. Two buffers have been implemented allowing a retry of reading the data.

FIG. 47 is a table illustrating a Slave's Read Results example response. The example response is a response to reading N+1 bytes. The indicated response is slave specific, such that slaves may send various data bit widths back as well which may be including Count and/or Command Codes. The response does not have to send back both the Command Code and Count. A response is given only if the Slave field (Master 2) is Unicast. No data is sent and no operations are performed with the ADC pointer if the Slave field is not Unicast.

FIG. 48 is a table illustrating a Master's Write command. The Address for placement of the value is set up via the Master's LSB RAM/REG Address command and the Master's MSB RAM/REG Address command. Before a value is written to any memory, the frame check sequence ("FCS") is checked first. The value field indicates the value that is written and the write command leaves the address off at the address where the write occurred. The slave will acknowledge the write with a command response as long as the FCS was correct.

FIG. 49 is a table illustrating a Master's LSB RAM/REG Address command. The Master's LSB RAM/REG Address command writes the RAM/Register Address Least Significant Byte Pointer. The Value field for the Master's LSB RAM/REG Address command will contain the RAM/Register LSB Address Pointer and for the command response, the slave will acknowledge the write as long as the FCS is correct.

FIG. 50 is a table illustrating a Master's MSB RAM/REG Address command. The Value field for the Master's MSB RAM/REG Address command will contain the RAM/Register MSB Address Pointer, and the slave will acknowledge the write as a command response as long as the FCS is correct.

FIG. 51 is a table illustrating the LSB EEPROM Address command. The LSB EEPROM Address command writes the EEPROM Address Least Significant Byte Pointer. The Value field contains the EEPROM LSB Address Pointer and the slave will acknowledge the write as a command response as long as the FCS is correct. The pointer Address will not change on a write that is NACK'd.

FIG. 52 is a table illustrating a MSB EEPROM Address command. The MSB EEPROM Address command writes the RAM/Register Address Most Significant Byte Pointer. The Value field contains the EEPROM MSB Address Pointer while the slave will acknowledge the write with a command response long as the FCS is correct. The pointer Address will not change on a write that is NACK'd.

FIG. 53 is a table illustrating a Master's Copy RAM/REG to EEPROM Memory command. This command can copy up to 256 bytes from RAM/Register Address Space to EEPROM address space. The EEPROM addresses are left off at the starting address as dictated by the commands LSB EEPROM Address and MSB EEPROM Address. RAM/Register addresses will be left off at their starting addresses as dictated by the commands LSB RAM/REG Address and MSB RAM/REG Address. The Unlocks command is sent as a guard against writing into the calibration constant and address areas of EEPROM. The slave will acknowledge the write with a command response as long as the FCS is correct. No action will be taken if the appropriate Unlocks command is not performed.

FIG. 54 is a table of a Master's Copy of EEPROM to RAM/REG Memory command. The Copying command copies up to 256 bytes from EEPROM Address Space to RAM/Register space. The EEPROM addresses will be left off at the starting address as dictated by the commands LSB EEPROM Address and MSB EEPROM Address. RAM/Register addresses will be left off at their starting addresses as dictated by the commands LSB RAM/REG Address and MSB RAM/REG Address. The Unlocks command must be sent as a guard against writing into sensitive areas of RAM/Register space. The slave will acknowledge the write with a command response as long as the FCS is correct. No action will be taken if the appropriate Unlocks command was not performed.

FIG. 55 is a table illustrating a Master's Quick Read command. This command reads address pointers that are not readable via a normal read using address pointers and also reads status words that are desirable for quick access.

FIG. 56 is a table illustrating a Master's Which Pointer to Read command and FIG. 57 is a table illustrating a Slave's Read Address Pointers Response command. The generalized Read command does not use these pointers because they are used for the Read itself. This command is useful for debug by checking if pointer manipulation is working properly.

As described above, in some embodiments of the invention an IMD provides power to a slave device by placing a DC bias voltage on the two-wire bus used for communication between the IMD and the slave device. However, two-wire buses according to the invention are in some cases exposed to conductive bodily fluids, particularly where the bus interfaces with the IMD and the slave device. In embodiments where DC bias powering is utilized, such exposure could, over time, lead to degradation and failure of the bus, or of metallic components of the IMD and slave device that are coupled to the bus, due to corrosion or the like.

Consequently, in preferred embodiments of the invention, an IMD provides power to a slave device by placing voltage pulses on the two-wire bus, which reduces the likelihood of failure due to corrosion or the like. Slave devices, such as sensor capsules 142 and 144 (FIG. 1) include recovery units 156 (FIG. 1) to recover power from the voltage pulses. In exemplary embodiments, recovery units 156 include rectifier circuits to recover power from the voltage pulses. In such embodiments, the two-wire bus may take any of the forms illustrated in FIGS. 4–7, as well as other forms.

Figure 58:
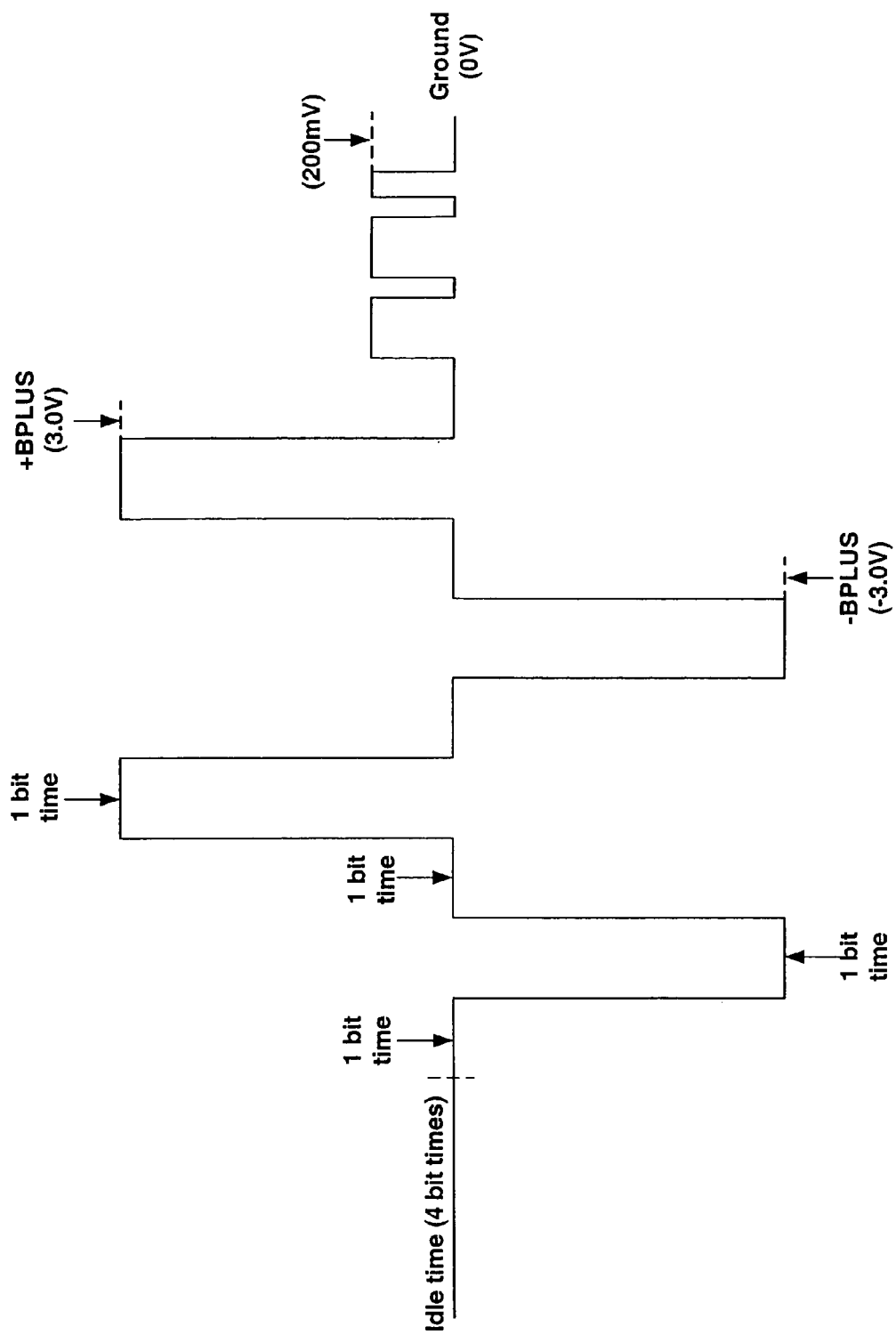
FIG. 58 illustrates power pulses and data pulses output by a master according to a pulsed power embodiment of the invention.

FIG. 58 illustrates power pulses and data pulses output by a master, e.g., an IMD, according to a pulsed power embodiment of the invention. In the illustrated embodiment, the master outputs voltage power pulses as bipolar voltage power pulse pairs. The duration of each pulse of the pair, of an interval between pulses of a pair, and of an interval between pulse pairs is illustrated as one bit time. As discussed above, one bit time is nominally equal to ten microseconds.

As illustrated in FIG. 58, there is no DC bias on the two-wire bus between the IMD and the slave devices. Data is communicated on the two-wire bus by variation of the voltage on one wire of the bus in the manner described above with reference to FIG. 13. However, in the illustrated embodiment, the variation is between a reference voltage, e.g., 0 V, and 200 mV. The amplitude of power pulses is the reference voltage +/−3.0 V.

However, the invention is not limited to the illustrated embodiment. Bipolar power pulse pairs can have any amplitude for the pulses, order of polarities of the pulses, duration of the pulses, and duration of the interval between the pulses of a pair. Further, bipolar power pulse pairs need not include an interval between the pulses of a pair. In some embodiments, power pulses are unipolar pulses, which can have any amplitude, duration, and polarity. In some embodiments, the master can vary the duration of voltage power pulses during operation of the IMD communication system.

A single power pulse, or, as illustrated in FIG. 58, a train of two or more voltage power pulses is delivered prior to communication of data. The first pulse of a train that follows a message on the bus is preceded by an idle period of five bit times in which the master holds the data line of the bus at the reference voltage, i.e., holds that line at a forced "0." The idle period includes four idle period bit times, and a fifth force "0" bit time attributed to the one force "0" bit time that precedes all delivered power pulses. In some embodiments, slave devices determine the polarity of data pulses based on the polarity of the immediately preceding power pulse, or of the second pulse of an immediately preceding bipolar power pulse pair. In exemplary embodiments, the master determines a number of power pulses to send before a message based on the power needed by the slave devices to perform the action requested by the message.

Slave devices wake-up from a low power state and monitor for a message Start sequence in response to detecting a power pulse on the bus. Single power pulses or trains of power pulses can be delivered without a message to follow, e.g., in order to maintain adequate power for the slave devices. In such cases, the pulse or pulse train is followed by an idle period of five bit times so that the slave devices can determine that no message is forthcoming and return to the low power state. In some embodiments, slave devices wake-up and perform a measurement or some other predetermined in response to detecting a power pulse on the bus, e.g., the slaves are triggered by a power pulse or sequence of power pulses as described above.

Figure 59:
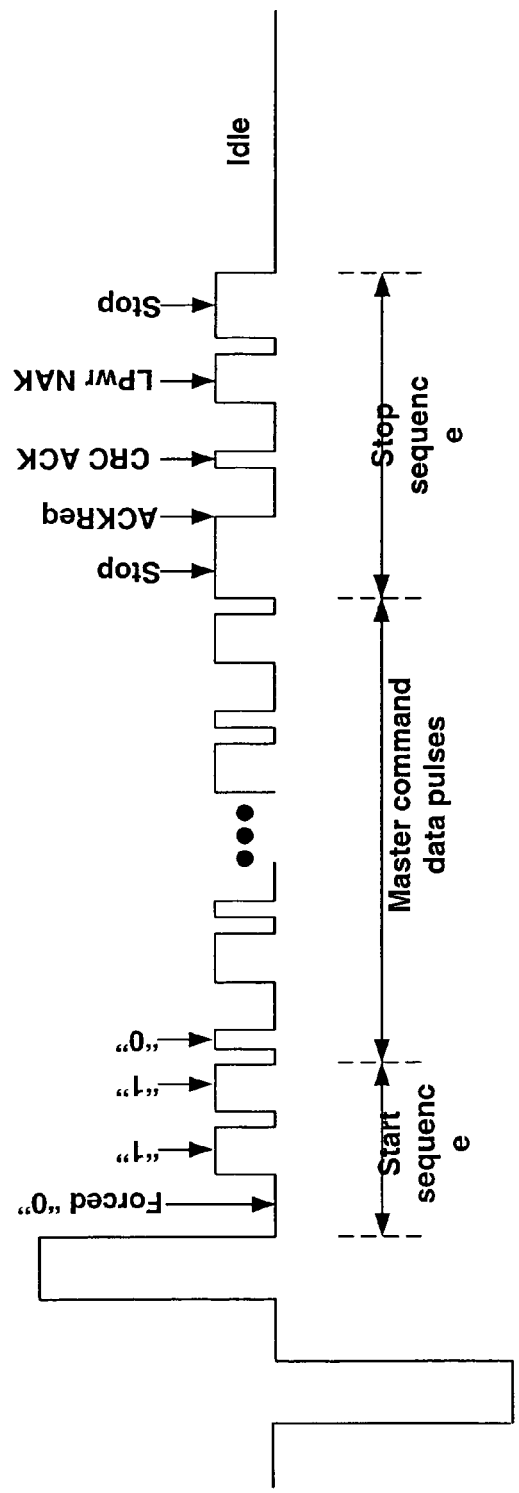
FIG. 59 illustrates an example message sequence for pulsed power embodiments of the invention.

FIG. 59 illustrates an example message sequence for pulsed power embodiments of the invention, which includes a Start sequence and command output by the master, and a master stop sequence. The Start sequence synchronizes the slaves to the master, and indicates that a command will be output by the master. In the illustrated example, the master outputs the Start sequence as a forced "0" followed by two logic "1's". In other embodiments, the start sequence is not preceded by any power pulses, but is streamed or chained with the end of a previous message, as will be described in greater detail below with reference to FIG. 60.

The Stop sequence includes a "Stop" and a master acknowledge request (ACKReq) output by the master, followed by a slave cyclical redundancy check acknowledge or non-acknowledge (CRC ACK/NAK) and slave low power acknowledge or non-acknowledge (LPwr ACK/NAK). The Stop sequence ends with a second "Stop" output by the master. The master outputs a "Stop" by holding the bus high continuously for 1 bit time.

As discussed above, slaves indicate a logic "0" by pulling the bus low at a shorter fraction of a bit time, and indicate a logic "1" by pulling the bus low at a longer fraction of the bit time. Consequently, in embodiments where the bus is shared by a plurality of slaves, output of a logic "0" by any of the slaves is detected as a logic "0" by the master for that bit time.

Slaves output a logic "0" during a CRC bit time of the Stop sequence to indicate a CRC ACK, i.e., to indicate that the command from the master is error-free according to the CRC error check contained in the Frame Check Sequence field of the command. If no slave outputs a logic "0", i.e., a CRC NAK is indicated, the command is resent. Where a CRC NAK is indicated, the master does not consider the LPwr ACK/NAK for that Stop sequence.

Slaves output a logic "0" during a LPwr bit time of the Stop sequence to indicate a low power status, e.g., to request delivery of additional power pulses from the master. If any slave outputs a logic "0", the master will detect a low power ACK, and determine that at least one slave has insufficient power. In some embodiments, the master outputs one or more power pulses in response to detection a low power ACK. If all slaves on the bus output a logic "1" or do not respond during the LPwr bit time, the master will detect a low power NAK.

In the example illustrated in FIG. 59, the master Stop sequence is followed by an idle period of at least five bit times that will precede another power pulse or train of power pulses. In other embodiments, the master Stop sequence is followed by slave data pulses, wherein a slave transmits information to the master, and a slave stop sequence. In such embodiments, the slave stop sequence is followed by an idle period that precedes another power pulse.

Figure 60:
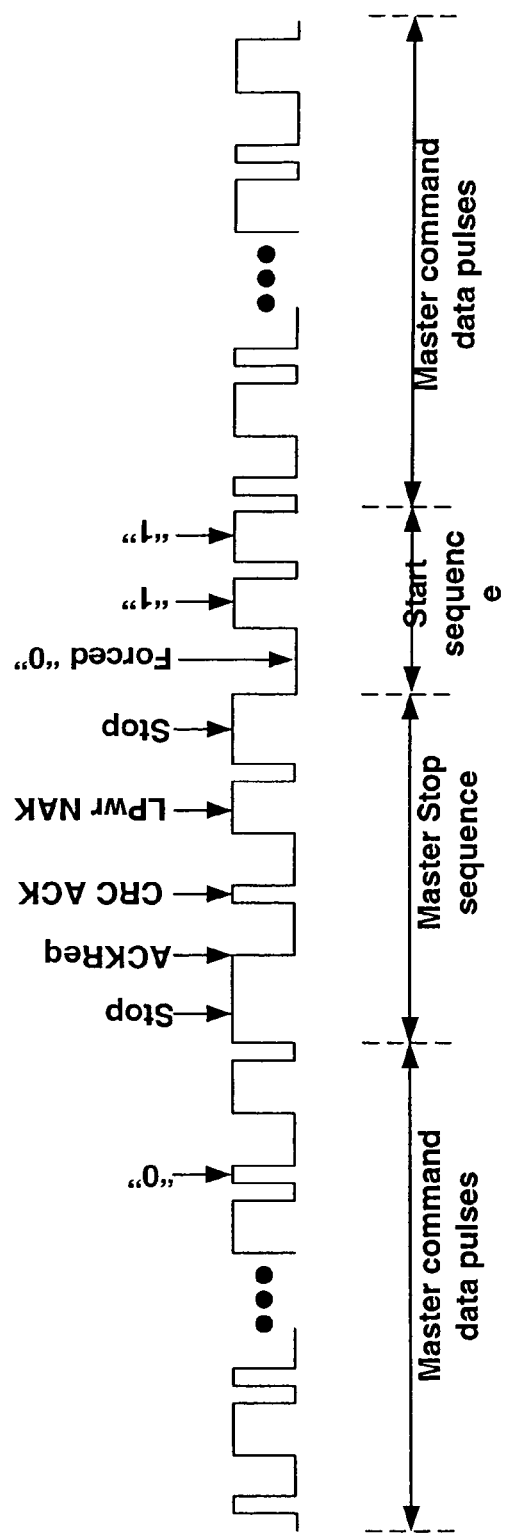
FIG. 60 illustrates delivery of a stream of messages between consecutive power pulses in accordance with some pulsed power embodiments of the invention.

In still other embodiments, as illustrated in FIG. 60, the master streams multiple messages, i.e., outputs multiple commands, between consecutive power pulses. Each command is preceded by a Start sequence, which alerts the sensors that an additional command will be sent, and synchronizes the sensor for receipt of the additional command. In some embodiments, one or more of the master Stop sequences within a message stream are followed by sensor data and sensor Stop sequences. A final "Stop" bit within a master or slave Stop sequence provides a rising edge, which is also used for resynchronization of the slave to prior to receipt of an additional command.

We claim:

1. An implantable medical device communication system, comprising:
an implantable medical device comprising a power supply, a controller, and a communication unit, wherein the communication unit combines data from the controller and power from the power supply to produce a communication signal that is selectively changeable between at least a first and a second voltage, produces a reference voltage, and generates voltage power pulses from the power supply;
a two-wire bus to receive the communication signal and the voltage power pulses on a first wire, and to receive the reference voltage on a second wire; and
a slave device comprising a recovery unit to recover power from the voltage power pulses and a transceiver unit to decode data from the selectively changeable communication signal transmitted across the first wire, wherein one bit time of data to be communicated across the first wire is defined as a predetermined number of clock cycles, a logic "0" is communicated by holding the first wire at the first voltage for a first fraction of the predetermined number of clock cycles, and a logic "1" is communicated by holding the first wire at the first voltage for a second fraction of the predetermined number of clock cycles, and wherein the second voltage is substantially equal to the reference voltage.

2. The implantable medical device communication system of claim 1, wherein the voltage power pulses comprise bipolar voltage power pulse pairs.

3. The implantable medical device communication system of claim 2, wherein the pulses of each bipolar voltage power pulse pair are separated by an interval, and a duration of the interval and of each of the pulses of each bipolar power pulse pair is substantially equal to one bit time.

4. The implantable medical device communication system of claim 1, wherein the slave device enters a power down state, detects one of the voltage power pulses, and exits the power down state based on detection of the voltage power pulse.

5. The implantable medical device communication system of claim 1, wherein the slave device detects at least one of the voltage power pulses, and performs a predetermined action based on detection of the voltage power pulse.

6. The implantable medical device communication system of claim 5, wherein the communication unit of the implantable medical device uses a sequence of voltage power pulses to address the slave device, and
wherein the slave device detects the sequence of voltage power pulses and performs the predetermined action based on detection of the sequence.

7. The implantable medical device communication system of claim 6, wherein the predetermined action comprises at least one of a measurement and delivery of a therapy.

8. The implantable medical device communication system of claim 1, wherein the communication unit of the implantable medical device outputs commands to the slave device.

9. The implantable medical device communication system of claim 8, wherein the communication unit of the implantable medical device outputs a start sequence subsequent to generation of one of the voltage power pulses, and outputs one of the commands subsequent to generation of the start sequence, and
wherein the transceiver unit of the slave device detects the voltage power pulse and monitors for the start sequence based on the detection.

10. The implantable medical device communication system of claim 9, wherein the transceiver unit of the slave device identifies a polarity of the voltage power pulse, and identifies a polarity of the first voltage for receipt of the start sequence and command based on the polarity of the voltage power pulse.

11. The implantable medical device communication system of claim 9, wherein the start sequence comprises three bit times, a first bit time of the start sequence comprises a forced "0" that is communicated by holding the first wire at the second voltage for substantially the entire first bit time, and each of a second bit time and third bit time of the start sequence comprise a logic "1".

12. The implantable medical device communication system of claim 9, wherein the communication unit outputs a plurality of commands to the slave device between consecutive voltage power pulses, and outputs a start sequence to precede each command.

13. The implantable medical device communication system of claim 9, wherein the transceiver unit of the slave device indicates a power status of the slave device to the implantable medical device during a bit time of a stop sequence that follows the command.

14. The implantable medical device communication system of claim 13, wherein the communication unit of the implantable medical device receives the indication of the power status from the transceiver unit of the slave device by driving the first wire of the bus at the first voltage, and then sensing the first wire to determine a fraction of the bit time at which the transceiver unit pulls the first wire to the second voltage.

15. The implantable medical device communication system of claim 14, wherein the transceiver unit of the slave device communicates a low power status by pulling the first wire to the second voltage at a first fraction of the bit time, and communicates an adequate power status by one of pulling the first wire to the second voltage at a second fraction of the bit time and allowing the first wire to remain substantially at the first voltage through the first and second fractions of the bit time.

16. The implantable medical device of claim 14, wherein the communication unit of the implantable medical device weakly holds the bus at the first voltage while sensing the first wire to determine a slave fraction of the bit time at which the transceiver unit pulls the first wire to the second voltage.

17. The implantable medical device communication system of claim 1, wherein the slave device comprises at least one of a sensor and an actuator that is external to the implantable medical device.

18. The implantable medical device communication system of claim 1, further comprising a plurality of slave devices, each slave device comprising a sonomicrometry transducer, wherein the communication unit of the implantable medical device directs at least one of the slave devices to act as a transmitter for a measurement and directs at least one of the slave devices to act as a receiver for the measurement.

19. The implantable medical device communication system of claim 1, wherein the implantable medical device comprises a first implantable medical device and the slave device comprises a second implantable medical device.

20. An implantable medical device communication system, comprising:
an implantable medical device comprising a power supply, a controller, and a communication unit, wherein the communication unit selectively outputs voltage power pulses and a plurality of different commands, each command preceded by a start sequence and followed by a stop sequence;
a bus to transmit the voltage power pulses and communicate the start sequences, stop sequences and the plurality of different commands; and
a slave device comprising a recovery unit to recover power from the voltage power pulses and a transceiver unit to receive the commands via the bus, wherein the transceiver unit indicates a power status of the slave device during the stop sequences.

21. The implantable medical device communication system of claim 20, wherein the stop sequence includes a plurality of bit times, and the transceiver unit indicates a low power status of the slave device by communicating a logic "0", and indicates an adequate power status of the slave device by either communicating a logic "1" or by not responding.

22. The implantable medical device communication system of claim 20, wherein the voltage power pulses comprise bipolar voltage power pulse pairs.

23. The implantable medical device communication system of claim 20, wherein the slave device enters a power down state, detects one of the voltage power pulses, and exits the power down state based on detection of the voltage power pulse.

24. The implantable medical device communication system of claim 20, wherein the slave device detects at least one of the voltage power pulses, and performs a predetermined action based on detection of the voltage power pulse.

25. The implantable medical device of claim 24,
wherein the communication unit of the implantable medical device uses a sequence of voltage power pulses to address the slave device, and
wherein the slave device detects the sequence of voltage power pulses and performs the predetermined action based on detection of the sequence.

26. The implantable medical device communication system of claim 20, wherein the communication unit outputs a plurality of commands to the slave device between consecutive voltage power pulses, and outputs a start sequence to precede each command.

27. The implantable medical device communication system of claim 20, wherein the communication unit outputs a plurality of voltage power pulses between consecutive commands.

28. The implantable medical device communication system of claim 20, wherein the slave device comprises a sensor that is external to the implantable medical device.

29. An implantable medical device communication system, comprising:

an implantable medical device comprising a power supply, a controller, and a communication unit, wherein the communication unit selectively outputs voltage power pulses and a plurality of different commands, and outputs a plurality of commands between consecutive voltage power pulses;

a bus to transmit the voltage power pulses and communicate the plurality of different commands; and a slave device comprising a recovery unit to recover power from the voltage power pulses and a transceiver unit to receive the commands via the bus.

30. The implantable medical device communication system of claim 29, wherein the communication unit outputs a start sequence to precede each command.

31. The implantable medical device communication system of claim 30, wherein the start sequence comprises three bit times, a first bit time of the start sequence comprises a forced "0", and each of a second bit time and third bit time of the start sequence comprise a logic "1".

32. The implantable medical device communication system of claim 29, wherein the communication unit outputs a plurality of voltage power pulses between consecutive commands.

* * * * *